US012655461B2

(12) United States Patent
Bandi et al.

(10) Patent No.: US 12,655,461 B2
(45) Date of Patent: Jun. 16, 2026

(54) BIOSENSORS FOR SELECTIVELY IDENTIFYING AZIDE IONS

(71) Applicant: Rutgers, The State University of New Jersey, New Brunswick, NJ (US)

(72) Inventors: Chandra Kanth Bandi, Piscataway, NJ (US); Shishir Chundawat, Piscataway, NJ (US); Kyle S. Skalenko, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 741 days.

(21) Appl. No.: 18/010,109

(22) PCT Filed: Jun. 28, 2021

(86) PCT No.: PCT/US2021/039368
§ 371 (c)(1),
(2) Date: Dec. 13, 2022

(87) PCT Pub. No.: WO2022/005966
PCT Pub. Date: Jan. 6, 2022

(65) Prior Publication Data
US 2023/0279464 A1 Sep. 7, 2023

Related U.S. Application Data

(60) Provisional application No. 63/045,907, filed on Jun. 30, 2020.

(51) Int. Cl.
*C12Q 1/40* (2006.01)
*C12N 15/70* (2006.01)
*C12Q 1/6897* (2018.01)
(52) U.S. Cl.
CPC .............. *C12Q 1/40* (2013.01); *C12N 15/70* (2013.01); *C12Q 1/6897* (2013.01); *C12Y 302/01018* (2013.01); *C12N 2800/101* (2013.01)

(58) Field of Classification Search
CPC ........ C12Q 1/40; C12Q 1/6897; C12N 15/70; C12N 2800/101; C12Y 302/01018
See application file for complete search history.

(56) References Cited

U.S. PATENT DOCUMENTS

2009/0269819 A1 10/2009 Filippov et al.

OTHER PUBLICATIONS

Bandi, et al., "Engineered Regulon to Enable Autonomous Azide Ion Biosensing, Recombinant Protein Production, and in Vivo Glycoengineering", ACS Synth Biol, vol. 10, Apr. 16, 2021, pp. 682-689.
Lamblin, et al., "Expression and Purification of the cynR Regulatory Gene Product: CynR Is a DNA-Binding Protein", J Bacteriol, vol. 175(24), 1993, pp. 7990-7999.
Lamblin, et al., "Functional Analysis of the *Escherichia coli* K-12 cyn Operon Transcriptional Regulation", J Bacteriol, vol. 176(21), 1994, pp. 6613-6622.
Sung, et al., "Characterization of the cyn Operon in *Escherichia coli* K12*", J Biol Chem, vol. 263, No. 29, Oct. 15, 1988, pp. 14769-14775.
PCT International Search Report and Written Opinion dated Oct. 22, 2021 for corresponding PCT International Application PCT/US2021/039368.

*Primary Examiner* — Abigail Vanhorn
*Assistant Examiner* — Stephanie L Sullivan
(74) *Attorney, Agent, or Firm* — Domingos J. Silva; Chihao Wang; SAUL EWING LLP

(57) ABSTRACT

The present disclosure provides, in one aspect, an azide-inducible system for controlled gene expression in *E. coli*. In another aspect, the present disclosure provides a high throughput screening method for the identification of new glycosynthases (e.g., mutant glycosyl hydrolases) with enhanced activity and unique substrate specificity.

14 Claims, 15 Drawing Sheets

Specification includes a Sequence Listing.

*cynT*
*(carbonic anhydrase)*

*cynS*
*(cyanate hydratase)*

*cynX*
*(cyanate transporter)*

*cynR* cynR cynR cynR inducer binding domain

■ cyanate     ■ azide $\bar{N}=C=O$     $\bar{N}=\overset{+}{N}=\bar{N}$

Affinity     Affinity

-2.4 kcal/mol     -2.7 kcal/mol

SEQUENCE LISTING

```
<160> NUMBER OF SEQ ID NOS: 39

<210> SEQ ID NO 1
<211> LENGTH: 111
<212> TYPE: DNA
<213> ORGANISM: Artificial sequence
<220> FEATURE:
<223> OTHER INFORMATION: Chemically synthesized

<400> SEQUENCE: 1
tcgcaaccta taagtaaatc caatggaact catcataaat gagactttta ccttatgaca      60
atcggcgagt agtctgcctc tcattccaga gacagacaga ggttaacgat g             111

<210> SEQ ID NO 2
<211> LENGTH: 332
<212> TYPE: DNA
<213> ORGANISM: Artificial sequence
<220> FEATURE:
<223> OTHER INFORMATION: Chemically synthesized

<400> SEQUENCE: 2
ggttcctcat taccgttatc atatgaacac accataacaa agatgcatgc agctgtctaa      60
atcccgcggc catggcggcc gggagcatgc gacgtcgggc ccaattcgcc cgatcttaat     120
gaatggccgg aagaggtacg gacgcgatat gcggggggtga gagggcaaat aggcaggttc    180
gccttcgtca cgctaggagg caattctata aggatcctcg caacctataa gtaaatccaa     240
tggaactcgt cagaaatgag acttttacct tatgacaatc ggctggtata atgcctctac     300
ttccagagac agacataagg agattacgca tg                                   332
```

-continued

```
<210> SEQ ID NO 3
<211> LENGTH: 229
<212> TYPE: DNA
<213> ORGANISM: Artificial sequence
<220> FEATURE:
<223> OTHER INFORMATION: Chemically synthesized

<400> SEQUENCE: 3
ggttcctcat taccgttatc atatgaacac accataacaa agatgcatgc agctgtctaa      60
atcccgcggc catggcggcc gggagcatgc gacgtcgggc ccaattcggg atcctcgcaa     120
cctataagta aatccaatgg aactcgtcag aaatgagact tttaccttat gacaatcggc     180
tggtataatg cctctacttc cagagacaga cataaggaga ttacgcatg                 229

<210> SEQ ID NO 4
<211> LENGTH: 1232
<212> TYPE: DNA
<213> ORGANISM: Artificial sequence
<220> FEATURE:
<223> OTHER INFORMATION: Chemically synthesized

<400> SEQUENCE: 4
ggttcctcat taccgttatc atatgaacac accataacaa agatgcatgc agctgtctaa      60
atcccgcggc catggcggcc gggagcatgc gacgtcgggc ccaattcgcc cgatcttaat     120
gaatggccgg aagaggtacg gacgcgatat gcgggggtga gagggcaaat aggcaggttc     180
gccttcgtca cgctaggagg caattctata agattggacc gtacgcatgt caaactgctg     240
gcgaaccgcg attccacgac cggtgcacga tttaactacg ccgacgtgac gacattcctg     300
ctaatgcctc gcccgccgga ccgccctcgt gatggggtag ctgggcatga ccttgtgaca     360
tataacgaga gtctacttgt ttaatcatct cacggcgaaa gtcggggga cagcagccgc      420 tgcagacatt ataccgcaac tacaccaagc tgagataact ccgtagttga ctacgcatcc     480
ctctaggcct tacttaaccg gatacagtga ctttgacagg tttgtgggct acagcaatca     540
cttgcatagc tgcgtatgga ggaagcaact cttgggtgtt agtatgttga ccctgtatt      600 agggatgcgg gtagtagatg tgggcagaga cacccaggtc aagtacacga ccctctcgta     660
ggaggtgttc cagatcacca taccaccata ccattcgagc atggcactat gtacgctgtc     720
cccattctgg tagtcatcat ccctatcacg gtttcgagtg actggtgacg gatatccccc     780
acgaatggag atcttattca cagtcggtca cattggagtg ctccttgact aatcagcttg     840
gccaggtctg ttgggcctcc gtgccccgag tttcggcgct gtgctgccga gagtcggcca     900
ttgtcattgg ggcctcactt gtggataccc cgacctattt tgacgggacc actcgcggta     960
gtcgttgggc ttatgcaccg tgaagtcctc cgccggcctc cccctacaa aagatgataa    1020 gctccggcaa gcaatattga acaacgcaag gatcggcgat ataaacagag aaacggctga    1080
ttactcttgt tggtgtggta tcgctaaact gggatcctcg caacctataa gtaaatccaa    1140
tggaactcgt cagaaatgag acttttacct tatgacaatc ggctggtata atgcctctac    1200
ttccagagac agacataagg agattacgca tg                                 1232

<210> SEQ ID NO 5
<211> LENGTH: 332
<212> TYPE: DNA
<213> ORGANISM: Artificial sequence
<220> FEATURE:
<223> OTHER INFORMATION: Chemically synthesized
```

<400> SEQUENCE: 5
ggttcctcat taccgttatc atatgaacac accataagga agatgcatgc agctgtctaa          60
atcccgcggc catggcggcc gggagcatgc gacgtcgggc ccaattcgcc cgatcttaat         120
gaatggccgg aagaggtacg gacgcgatat gcggggtga gagggcaaat aggcaggttc          180
gccttcgtca cgctaggagg caattctata aggatcctcg caacctataa gtaaatccaa         240
tggaactcgt cagaaatgag acttttacct tatgacaatc ggctggtata atgcctctac         300
ttccagagac agacataagg agattacgca tg                                       332

<210> SEQ ID NO 6
<211> LENGTH: 332
<212> TYPE: DNA
<213> ORGANISM: Artificial sequence
<220> FEATURE:
<223> OTHER INFORMATION: Chemically synthesized

<400> SEQUENCE: 6
ggttcctcat taccgttatc atatgaacac gccataagga agatgcatgc agctgtctaa          60
atcccgcggc catggcggcc gggagcatgc gacgtcgggc ccaattcgcc cgatcttaat         120
gaatggccgg aagaggtacg gacgcgatat gcggggtga gagggcaaat aggcaggttc          180
gccttcgtca cgctaggagg caattctata aggatcctcg caacctataa gtaaatccaa         240
tggaactcgt cagaaatgag acttttacct tatgacaatc ggctggtata atgcctctac         300
ttccagagac agacataagg agattacgca tg                                       332

<210> SEQ ID NO 7
<211> LENGTH: 333
<212> TYPE: DNA
<213> ORGANISM: Artificial sequence
<220> FEATURE:
<223> OTHER INFORMATION: Chemically synthesized

<400> SEQUENCE: 7
gttcctcatt accgttatca tatgaacaca ccataaggaa aagatgcatg cagctgtcta          60
aatcccgcgg ccatggcggc cgggagcatg cgacgtcggg cccaattcgc cgatcttaa          120 tgaatggccg gaagaggtac ggacgcgata tgcggggtg agagggcaaa taggcaggtt         180
cgccttcgtc acgctaggag gcaattctat aaggatcctc gcaacctata agtaaatcca         240
atggaactcg tcagaaatga gactttacc ttatgacaat cggctggtat aatgcctcta         300
cttccagaga cagacataag gagattacgc atg                                      333

<210> SEQ ID NO 8
<211> LENGTH: 336
<212> TYPE: DNA
<213> ORGANISM: Artificial sequence
<220> FEATURE:
<223> OTHER INFORMATION: Chemically synthesized

<400> SEQUENCE: 8
ggagagttcc tcattaccgt tatcatatga acacaccata aggaagatgc atgcagctgt          60
ctaaatcccg cggccatggc ggccgggagc atgcgacgtc gggcccaatt cgcccgatct         120
taatgaatgg ccggaagagg tacggacgcg atatgcgggg gtgagagggc aaataggcag         180
gttcgccttc gtcacgctag gaggcaattc tataaggatc ctcgcaacct ataagtaaat         240
ccaatggaac tcgtcagaaa tgagactttt accttatgac aatcggctgg tataatgcct         300
ctacttccag agacagacat aaggagatta cgcatg                                   336

-continued

<210> SEQ ID NO 9
<211> LENGTH: 74
<212> TYPE: DNA
<213> ORGANISM: Artificial sequence
<220> FEATURE:
<223> OTHER INFORMATION: Chemically synthesized

<400> SEQUENCE: 9
tgataagcgt agcgcatcag gcaattccag ccgcagacct gtgtcagcgg gtgtaggctg      60
gagctgcttc gaag                                                       74

<210> SEQ ID NO 10
<211> LENGTH: 74
<212> TYPE: DNA
<213> ORGANISM: Artificial sequence
<220> FEATURE:
<223> OTHER INFORMATION: Chemically synthesized

<400> SEQUENCE: 10
tctacattag ccgcatccgg catgaacaaa gcgcaggaac aagcgtcgca catatgaata      60
tcctccttag ttcc                                                       74

<210> SEQ ID NO 11
<211> LENGTH: 39
<212> TYPE: DNA
<213> ORGANISM: Artificial sequence
<220> FEATURE:
<223> OTHER INFORMATION: Chemically synthesized

<400> SEQUENCE: 11
aaccaggata atgatacaga ttaaatcaga acgcagaag                            39

<210> SEQ ID NO 12
<211> LENGTH: 32
<212> TYPE: DNA
<213> ORGANISM: Artificial sequence
<220> FEATURE:
<223> OTHER INFORMATION: Chemically synthesized

<400> SEQUENCE: 12
ttgtaatcga taacgtaaat gcatgccgct tc                                   32

<210> SEQ ID NO 13
<211> LENGTH: 34
<212> TYPE: DNA
<213> ORGANISM: Artificial sequence
<220> FEATURE:
<223> OTHER INFORMATION: Chemically synthesized

<400> SEQUENCE: 13
gcatttacgt tatcgattac aaacgttgaa cgac                                 34

<210> SEQ ID NO 14
<211> LENGTH: 32
<212> TYPE: DNA
<213> ORGANISM: Artificial sequence
<220> FEATURE:
<223> OTHER INFORMATION: Chemically synthesized

<400> SEQUENCE: 14
aatctgtatc attatcctgg ttctttcccc ca                                   32

<210> SEQ ID NO 15

-continued

```
<211> LENGTH: 28
<212> TYPE: DNA
<213> ORGANISM: Artificial sequence
<220> FEATURE:
<223> OTHER INFORMATION: Chemically synthesized

<400> SEQUENCE: 15
cggtggcagc tccaaaggtg aagaactg                                      28

<210> SEQ ID NO 16
<211> LENGTH: 29
<212> TYPE: DNA
<213> ORGANISM: Artificial sequence
<220> FEATURE:
<223> OTHER INFORMATION: Chemically synthesized

<400> SEQUENCE: 16
aatgaggaac catgctctct cgacatatc                                     29

<210> SEQ ID NO 17
<211> LENGTH: 36
<212> TYPE: DNA
<213> ORGANISM: Artificial sequence
<220> FEATURE:
<223> OTHER INFORMATION: Chemically synthesized

<400> SEQUENCE: 17
cgagagagca tggttcctca ttaccgttat catatg                             36

<210> SEQ ID NO 18
<211> LENGTH: 23
<212> TYPE: DNA
<213> ORGANISM: Artificial sequence
<220> FEATURE:
<223> OTHER INFORMATION: Chemically synthesized

<400> SEQUENCE: 18
cctttggagc tgccaccgcc atg                                           23

<210> SEQ ID NO 19
<211> LENGTH: 40
<212> TYPE: DNA
<213> ORGANISM: Artificial sequence
<220> FEATURE:
<223> OTHER INFORMATION: Chemically synthesized

<400> SEQUENCE: 19
cgggcccaat tcgggatcct cgcaacctat aagtaaatcc                         40

<210> SEQ ID NO 20
<211> LENGTH: 27
<212> TYPE: DNA
<213> ORGANISM: Artificial sequence
<220> FEATURE:
<223> OTHER INFORMATION: Chemically synthesized

<400> SEQUENCE: 20
cgaggatccc gaattgggcc cgacgtc                                       27

<210> SEQ ID NO 21
<211> LENGTH: 31
<212> TYPE: DNA
<213> ORGANISM: Artificial sequence
<220> FEATURE:
<223> OTHER INFORMATION: Chemically synthesized

<400> SEQUENCE: 21
```

-continued cgctaaactg ggatcctcgc aacctataag t                                     31

<210> SEQ ID NO 22
<211> LENGTH: 36
<212> TYPE: DNA
<213> ORGANISM: Artificial sequence
<220> FEATURE:
<223> OTHER INFORMATION: Chemically synthesized

<400> SEQUENCE: 22
gtacggtcca atcttataga attgcctcct agcgtg                                36

<210> SEQ ID NO 23
<211> LENGTH: 31
<212> TYPE: DNA
<213> ORGANISM: Artificial sequence
<220> FEATURE:
<223> OTHER INFORMATION: Chemically synthesized

<400> SEQUENCE: 23
caattctata agattggacc gtacgcatgt c                                     31

<210> SEQ ID NO 24
<211> LENGTH: 31
<212> TYPE: DNA
<213> ORGANISM: Artificial sequence
<220> FEATURE:
<223> OTHER INFORMATION: Chemically synthesized

<400> SEQUENCE: 24
gcgaggatcc cagtttagcg ataccacacc a                                     31

<210> SEQ ID NO 25
<211> LENGTH: 32
<212> TYPE: DNA
<213> ORGANISM: Artificial sequence
<220> FEATURE:
<223> OTHER INFORMATION: Chemically synthesized

<400> SEQUENCE: 25
atgaacacac cataaggaag atgcatgcag ct                                    32

<210> SEQ ID NO 26
<211> LENGTH: 32
<212> TYPE: DNA
<213> ORGANISM: Artificial sequence
<220> FEATURE:
<223> OTHER INFORMATION: Chemically synthesized

<400> SEQUENCE: 26
agctgcatgc atcttcctta tggtgtgttc at                                    32

<210> SEQ ID NO 27
<211> LENGTH: 33
<212> TYPE: DNA
<213> ORGANISM: Artificial sequence
<220> FEATURE:
<223> OTHER INFORMATION: Chemically synthesized

<400> SEQUENCE: 27
gttatcatat gaacacgcca taaggaagat gca                                   33

<210> SEQ ID NO 28
<211> LENGTH: 33
<212> TYPE: DNA

-continued

```
<213> ORGANISM: Artificial sequence
<220> FEATURE:
<223> OTHER INFORMATION: Chemically synthesized

<400> SEQUENCE: 28
tgcatcttcc ttatggcgtg ttcatatgat aac                                    33

<210> SEQ ID NO 29
<211> LENGTH: 40
<212> TYPE: DNA
<213> ORGANISM: Artificial sequence
<220> FEATURE:
<223> OTHER INFORMATION: Chemically synthesized

<400> SEQUENCE: 29
catatgaaca caccataagg aaaagatgca tgcagctgtc                              40

<210> SEQ ID NO 30
<211> LENGTH: 40
<212> TYPE: DNA
<213> ORGANISM: Artificial sequence
<220> FEATURE:
<223> OTHER INFORMATION: Chemically synthesized

<400> SEQUENCE: 30
gacagctgca tgcatctttt ccttatggtg tgttcatatg                              40

<210> SEQ ID NO 31
<211> LENGTH: 27
<212> TYPE: DNA
<213> ORGANISM: Artificial sequence
<220> FEATURE:
<223> OTHER INFORMATION: Chemically synthesized

<400> SEQUENCE: 31
agagttcctc attaccgtta tcatatg                                           27

<210> SEQ ID NO 32
<211> LENGTH: 24
<212> TYPE: DNA
<213> ORGANISM: Artificial sequence
<220> FEATURE:
<223> OTHER INFORMATION: Chemically synthesized

<400> SEQUENCE: 32
ctctccatgc tctctcgaca tatc                                              24

<210> SEQ ID NO 33
<211> LENGTH: 1365
<212> TYPE: DNA
<213> ORGANISM: Artificial sequence
<220> FEATURE:
<223> OTHER INFORMATION: Chemically synthesized

<400> SEQUENCE: 33
atcgattaca aacgttgaac gactgggtta cagcgagctt agtttatgcc ggatgcggcg       60
tgaacgcctt atccggccta cgtagagcac tgaactcgta ggcctgataa gcgtagcgca      120
tcaggcaatt ccagccgctg atctgtgtca gcggctaccg tgattcattc cgccaacaa       180 ccgcgcattc ctccaacgcc atgtgcaaaa atgccttcgc agcggctgtc tgccagctgt      240
agtttatgcc ggatgcggcg tgaacgcctt atccggccta cgtagagcac tgaactcgta      300
ggcctgataa gcgtagcgca tcaggcaatt ccagccgcag acctgtgtca gcggctaccg      360
tgattcattt ccgccaacaa ccgcgcattt atccaacgcc atgtgcaaaa atgccttcgc      420
```

-continued

```
ggcggctgtc tgccagctat ttttccgccg caacaaaacc gccgttctct ccagtagtgg       480
cggggcaaga gaaatagctt taagcccgtc atgttgtgtg gcaatcgctg ctggtaacaa       540
tgtggaaagg gaagtgcggc gaatcagctc cagaaccgcg ctaattgagt tcgcctcaat       600
gaccacctgt ggatgtagcc ccgctttctc gcagtagtgg tcaatttgct ctctggtggc       660
aaattccgcg ctgagcagga ccagtttttc atcatgcaag cgactcaacg ccacctgttc       720
atggacggcc agcggatgat gttgcgccac gactaacgct aaactttctg tcagtaaagg       780
aattgcctcc agctccggcg aatgcacagg cgcgaaggca tcccaacgt ccaactcgtc        840 gcggcaaagc atatcctcga ttttctcctg cgacatttcc tgtagctgga gcgtgatgct       900
gggatagcgc gcatagaaat ccgccattaa ggggccgata aagtagctcg taaaggtggg       960
ggtgacggcg atacgcagcg atcctcgcgt cagatcggca acatcatgaa tcgcccgttt      1020
acccgccccc agttcctgta acgcccggct ggcgtactgt cgccagactt ctcctgcatc      1080
agtgagacga atcgttcgcc cgctacggtc aaacagcggc acgcctaaac tctcctctaa      1140
ctggcgaatc tgctgggaaa gcgcaggttg ggagacgtgc aacgcactgg cggcacgggt      1200
gaagctgcca tgttcagcca cggcaagaaa ataattgata tgtcgagaga gcattcgcaa      1260
cctataagta aatccaatgg aactcatcat aaatgagact tttaccttat gacaatcggc      1320
gagtagtctg cctctcattc cagagacaga cagaggttaa cgatg                      1365

<210> SEQ ID NO 34
<211> LENGTH: 368
<212> TYPE: DNA
<213> ORGANISM: Artificial sequence
<220> FEATURE:
<223> OTHER INFORMATION: Chemically synthesized

<400> SEQUENCE: 34
ggttcctcat taccgttatc atatgaacac accataacaa agatgcatgc agctgtctaa        60
atcccgcggc catggcggcc gggagcatgc gacgtcgggc ccaattcgcc cgatcttaat       120
gaatggccgg aagaggtacg gacgcgatat gcggggtga gagggcaaat aggcaggttc        180
gccttcgtca cgctaggagg caattctata aggatcctcg caacctataa gtaaatccaa       240
tggaactcgt cagaaatgag acttttacct tatgacaatc ggctggtata atgcctctac       300
ttccagagac agacataagg agattacgca tgcatcacca tcatcaccat caccatggcg       360
gtggcagc                                                              368

<210> SEQ ID NO 35
<211> LENGTH: 900
<212> TYPE: DNA
<213> ORGANISM: Artificial sequence
<220> FEATURE:
<223> OTHER INFORMATION: Chemically synthesized

<400> SEQUENCE: 35
gattggaccg tacgcatgtc aaactgctgg cgaaccgcga ttccacgacc ggtgcacgat        60
ttaactacgc cgacgtgacg acattcctgc taatgcctcg cccgccggac cgccctcgtg       120
atggggtagc tgggcatgac cttgtgacat ataacgagag tctacttgtt taatcatctc       180
acggcgaaag tcgggggggac agcagccgct gcagacatta taccgcaact acaccaagct      240
gagataactc cgtagttgac tacgcatccc tctaggcctt acttaaccgg atacagtgac       300
tttgacaggt ttgtgggcta cagcaatcac ttgcatagct gcgtatggag gaagcaactc      360
```

-continued

```
ttgggtgtta gtatgttgac ccctgtatta gggatgcggg tagtagatgt gggcagagac      420
acccaggtca agtacacgac cctctcgtag gaggtgttcc agatcaccat accaccatac      480
cattcgagca tggcactatg tacgctgtcc ccattctggt agtcatcatc cctatcacgg      540
tttcgagtga ctggtgacgg atatccccca cgaatggaga tcttattcac agtcggtcac      600
attggagtgc tccttgacta atcagcttgg ccaggtctgt tgggcctccg tgccccgagt      660
ttcggcgctg tgctgccgag agtcggccat tgtcattggg gcctcacttg tggatacccc      720
gacctatttt gacgggacca ctcgcggtag tcgttgggct tatgcaccgt gaagtcctcc      780
gccggcctcc cccctacaaa agatgataag ctccggcaag caatattgaa caacgcaagg      840
atcggcgata taaacagaga aacggctgat tactcttgtt ggtgtggtat cgctaaactg      900
```

```
<210> SEQ ID NO 36
<211> LENGTH: 115
<212> TYPE: DNA
<213> ORGANISM: Artificial sequence
<220> FEATURE:
<223> OTHER INFORMATION: Chemically synthesized

<400> SEQUENCE: 36
tcgcaaccta taagtaaatc caatggaact cgtcagaaat gagactttta ccttatgaca       60
atcggctggt ataatgcctc tacttccaga gacagacata aggagattac gcatg          115
```

```
<210> SEQ ID NO 37
<211> LENGTH: 62
<212> TYPE: DNA
<213> ORGANISM: Artificial sequence
<220> FEATURE:
<223> OTHER INFORMATION: Chemically synthesized

<400> SEQUENCE: 37
tagacagctg catgcatctt tgttatggtg tgttcatatg ataacggtaa tgaggaacca       60
tg                                                                       62
```

```
<210> SEQ ID NO 38
<211> LENGTH: 115
<212> TYPE: DNA
<213> ORGANISM: Artificial sequence
<220> FEATURE:
<223> OTHER INFORMATION: Chemically synthesized

<400> SEQUENCE: 38
tcgcaaccta taagtaaatc caatggaact cgtcagaaat gagactttta ccttatgaca       60
atcggctggt ataatgcctc tacttccaga gacagacata aggagattac gcatg          115
```

```
<210> SEQ ID NO 39
<211> LENGTH: 66
<212> TYPE: DNA
<213> ORGANISM: Artificial sequence
<220> FEATURE:
<223> OTHER INFORMATION: Chemically synthesized

<400> SEQUENCE: 39
tagacagctg catgcatctt ccttatggtg tgttcatatg ataacggtaa tgaggaactc       60
tccatg                                                                   66
```

BIOSENSORS FOR SELECTIVELY IDENTIFYING AZIDE IONS

CROSS REFERENCE TO RELATED APPLICATIONS

The present application is a 35 U.S.C. § 371 national phase application of, and claims priority to, International Application No. PCT/US2021/039368, filed Jun. 28, 2021, which claims priority under 35 U.S.C. § 119(e) to U.S. Provisional Patent Application No. 63/045,907, filed Jun. 30, 2020, all of which are incorporated herein by reference in their entireties.

STATEMENT REGARDING FEDERALLY SPONSORED RESEARCH

This invention was made with government support under grant numbers 1704679 and 1904890 awarded by the National Science Foundation. The government has certain rights in this invention.

SEQUENCE LISTING

The present application contains a sequence listing which has been submitted in ASCII format and is hereby incorporated by reference in its entirety. The ASCII txt file, created on Jun. 27, 2021 and amended on Jun. 21, 2023, is named "370602-7016US1 Replacement Sequence Listing ST25.txt" and is 16 kilobytes in size.

BACKGROUND

The azide is a versatile functional group which may exist as an inorganic salt or as a substituent of an organic compound, both of which forms have been exploited in a number of applications in everyday life, as well as laboratory research. Azide ions are used in automobile airbags, detonators, pesticides, and chemical preservatives. Similarly, organic azides have received considerable attention in chemistry, biology and material sciences. Azido linked substrates are good precursor molecules for the synthesis of organic compounds, natural products, modified carbohydrates, and polymer cross-linkers. Several azido polymers are used as energetic binders and plasticizers to increase the mechanical and thermal properties of materials. Azide modification to enzyme inhibitors such as colecoxib, rofecoxib and chloramphenicol has improved their inhibitory potency. Many azido containing drugs such as azidamfenicol, azidocillin, and zidovudine are also clinically approved for oral use. The importance of azide functionalized sugars (e.g., glycosyl azides and fucosyl azides) are increasing tremendously, especially for carbohydrate synthesis and glycobiology. With the development of biorthogonal "click chemistry," glycosyl azides are routinely used for dynamic imaging of biomolecules in living systems to understand their function, localization, and pathway regulation (Proc. Natl. Acad. Sci. 2007, 104:16793-16797).

Release of an azide ion inside cells can pose a safety risk as a result of their inherent toxicity, and may further interfere with reactions involving organic azides. Thus, assays which may detect in vivo release of azides may permit improved control in the application of organic azides. Currently, there are no in vivo detection methods to selectively identify inorganic (free) azide ion from the background of organic azides. Several sensitive in vitro techniques involving spectrophotometry, fluorescence, mass spectrometry, and redox sensing have been developed to identify free azide, but no study has compared their selectivity against chemically linked azides (i.e., organic azides).

Therefore, there is a need in the art for in vivo cell-based azide biosensors, and methods using the same, to selectively identify azide ions. The present disclosure addresses this need.

BRIEF SUMMARY

The present disclosure relates, in part, to a construct comprising a cyn promoter comprising an engineered −10 sequence and a consensus ribosome binding sequence; which is linked to a cynR promoter comprising an engineered −10 sequence, wherein the engineered −10 sequences comprise at least one nucleotide addition, subtraction, and/or mutation that improves protein expression from the respective promoters.

In another aspect, the present disclosure provides a plasmid vector comprising a construct of the present disclosure, an ampicillin resistance gene, and a gene encoding a protein of interest, wherein the gene is located downstream of the cyn promoter, wherein the expression of the gene encoding the protein of interest is inducible by an azide or a cyanate.

In another aspect, the present disclosure provides an inducible protein expression system for enhancing the expression of a protein of interest, wherein the protein expression system comprises a host cell transformed with a plasmid vector of the present disclosure. In certain embodiments, the protein of interest is a reporter protein. In certain embodiments, the reporter protein is GFP.

In another aspect, the present disclosure provides a tunable synthetic biosensor for in vivo detection of an inorganic azide, wherein the biosensor comprises a protein expression system of the present disclosure.

In another aspect, the present disclosure provides a method of screening activity and specificity of an enzyme in an enzymatic reaction that generates an azide ion, wherein the method comprises contacting a biosensor of the present disclosure with the azide ion generated during the enzymatic reaction, wherein the protein of interest is a reporter protein, and quantifying a signal generated from the reporter protein, wherein the quantified signal is positively correlated with the activity and the specificity of the enzyme.

BRIEF DESCRIPTION OF THE DRAWINGS

The following detailed description of specific embodiments of the disclosure will be better understood when read in conjunction with the appended drawings. For the purpose of illustrating the disclosure, exemplary embodiments are shown in the drawings. It should be understood, however, that the disclosure is not limited to the precise arrangements and instrumentalities of the embodiments shown in the drawings.

FIG. 1A shows that the cynTSX operon is present in the *E. coli* genome to facilitate its growth in cyanate-containing environments. Cyanate molecules bind to the cynR repressor protein which regulates the protein expression of three essential genes (cynT, cynS, cynX). FIG. 1B shows docking of cyanate and azide in the binding pocket of cynR protein. Since azide is a structural homolog for cyanate, it binds well in the cynR binding pocket and in the same location as cyanate. FIG. 1C is plasmid map of pCyn-v1-GFP containing the native cynR and cyn operator region cloned upstream of a GFP reporter gene. The native version (v1) was used for GFP expression using azide and cyanate molecules. FIG. 1D is a flow cytometer analysis of in vivo GFP expression induced by cyanate and azide in BW25113-wt and BW25113-sCB1 strains.

FIG. 2A shows E. coli BW25113 wild type and the knockout strains. $P_{cynR}$ and $P_{cynTSX}$ are the promoters for cynR and cynTSX genes. Individual genes are color coded and the knocked out genes are illustrated with "X" marks. FIGS. 2B and 2C show plasmid maps of pCyn-v2-GFP (FIG. 2B) and pCyn-v8-GFP (FIG. 2C) containing the engineered regulatory region between cynR and GFP genes. The mutational replacements in the promoter region are represented by asterisks (*) and additions are denoted by plus signs (+). FIG. 2D shows bar graphs showing the GFP fluorescence of the bulk cell lysates of engineered strains containing three plasmid variants (v1, v2, v8). The inset graph illustrates GFP fluorescence measured for the native promoter construct (pCyn-v1-GFP). FIG. 2E shows the fluorescence plot for cell lysate of BW25113-wt strain containing pCyn-v2-GFP and induced with different concentrations of sodium azide.

FIG. 3A shows that E. coli BW25113-Wt cells containing the pCyn-v2-GFP plasmid were induced with varying azide concentrations for 24 hours and GFP fluorescence of cell lysates was measured at various time points. FIG. 3B shows that E. coli BL21 cells containing the pEC-GFP plasmid were induced with different IPTG concentrations for 24 hours and GFP fluorescence of the cell lysate was measured at different time points. FIG. 3C shows a diagram (top) illustrating that azide ions are released from 1-Glc-N$_3$ but not 2-Glc-N$_3$ in the bacterial cells. E. coli BW25113-Wt cells with the pCyn-v2-GFP plasmid were incubated with 1-Glc-N$_3$ and 2-Glc-N$_3$ and the GFP fluorescence of the respective cell lysates are shown as a bar graph (bottom). The inset contains the flow cytometry analysis of the cells incubated with 1-Glc-N$_3$ for 4 hours.

FIG. 10A provides a schematic of E. coli comprising two plasmids (pEC-TmAfc and pCyn-v2-GFP), incubated with glycosynthase reaction substrates, fucosyl azide (triangle) and pNP-xylose (star). TmAfc-D224G mutant alone catalyzes the glycosynthase (GS) reaction, releasing azide ion as a by-product, which then induces the azide promoter on the secondary plasmid (pCyn-v2-GFP) resulting in GFP expression. FIG. 10B provides a flow cytometry analysis of E. coli cells containing dual plasmids were incubated under a number of unique conditions, wherein only cells expressing TmAfc-D224G mutant in the presence of both the GS reaction donor/ acceptor sugar substrates provided a clear shift in cell fluorescence.

DETAILED DESCRIPTION

Figure 1A:
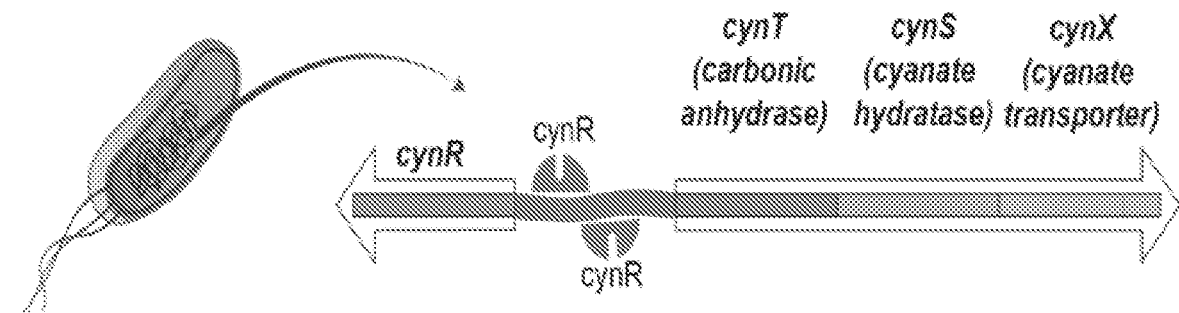
FIGS. 1A-1D illustrate promoter engineering to improve the GFP expression using azide and cyanate inducers.

Azide detection inside the cells is critical to the study biotoxicity, stability of pharmaceutical azido-drugs, and carbohydrate active enzyme engineering. Several techniques have been developed to detect the presence of azide ions in the system. However, these techniques are either applicable only to in vitro based study or require expensive sensing reagents or cannot selectively identify only inorganic azide. The present disclosure provides an in vivo cell based azide biosensor for the selective detection of azide ions. In certain embodiments, a cyanate/azide ion inducible promoter regulating the expression of green fluorescent protein (GFP) is engineered. In certain embodiments, the promoter is optimized further to improve GFP expression inside E. coli cells. The application of this synthetic promoter as alternative protein expression system and as tool for enzyme engineering is described herein.

Definitions

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, selected materials and methods are described herein. In describing and claiming the present disclosure, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Encoding" refers to the inherent property of specific sequences of nucleotides in a polynucleotide, such as a gene or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the noncoding strand (i.e., template strand), used as the template for transcription of a gene, can be referred to as encoding the protein or other product of that gene.

The term "expression" as used herein is defined as the transcription and/or translation of a particular nucleotide sequence driven by its promoter and/or ribosome binding site.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

The term "knockdown" as used herein refers to a decrease in gene expression of one or more genes.

The term "knockout" as used herein refers to the ablation of gene expression of one or more genes.

By the term "modified" or "engineered" as used herein, is meant a changed state or structure of a molecule or cell of the disclosure. Molecules may be modified in many ways, including chemically, structurally, and functionally. Cells may be modified through the introduction of nucleic acids.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "promoter" as used herein is defined as a DNA sequence recognized by the synthetic machinery of the cell (e.g., RNA polymerase), or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

The term "ribosome binding sequence" or RBS, also called a "Shine-Dalgarno sequence" or SD sequence, is a series of nucleotides upstream of the start codon of a messenger RNA (mRNA) sequence, which allows the binding of ribosomes and the initiation of translation. Ribosome binding sequences are typically features of prokaryotic mRNA, however eukaryotic ribosome complexes can interact with similar internal ribosome entry sites (IRES) commonly found in viral and engineered mRNA molecules.

The term "consensus" or "consensus sequence" as used herein refers to a sequence of DNA, RNA, or protein that represents the most common or ideal sequence for a particular feature or motif. Consensus sequences are determined statistically by the alignment of similar sequence features across a large number of genes and/or species in order to determine the most common nucleotide or amino acid at each position. As such, a consensus sequence of a particular feature or motif often represents a highly efficient or optimized sequence for a particular feature or motif.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996);

"Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the disclosure, and, as such, may be considered in making and practicing the disclosure. Particularly useful techniques for particular embodiments will be discussed in the sections that follow.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DESCRIPTION

The *E. coli* genome consists of several operons (630-700), which are essential for bacterial metabolism, performing specific functions key for survival in harsh environments. One such operon enables *E. coli* to overcome the toxicity of exogenous cyanate and survive in cyanate-rich environments. In *E. coli*, this operon, called the cyn operon, contains three genes; cynT, cynS and cynX (FIG. 1A), which encode carbonic anhydrase, cyanate hydratase, and cyanate transporter proteins. The cyanate hydratase catalyzes the bicarbonate-dependent decomposition of cyanate into carbon dioxide and ammonia. This process decreases the concentration of cyanate inside the cells. The cyn operon is activated when the cyanate molecule binds to the repressor protein bound to the cyn promote/operator region. The operon is under the regulation of a cynR repressor protein which upon binding to the operator region results in unfavorable DNA bending. The exogenous cyanate binds to the cynR inducer binding domain and causes conformational changes in the DNA binding domain thereby reducing the bend in the operator region and facilitating transcription.

Figure 1B:
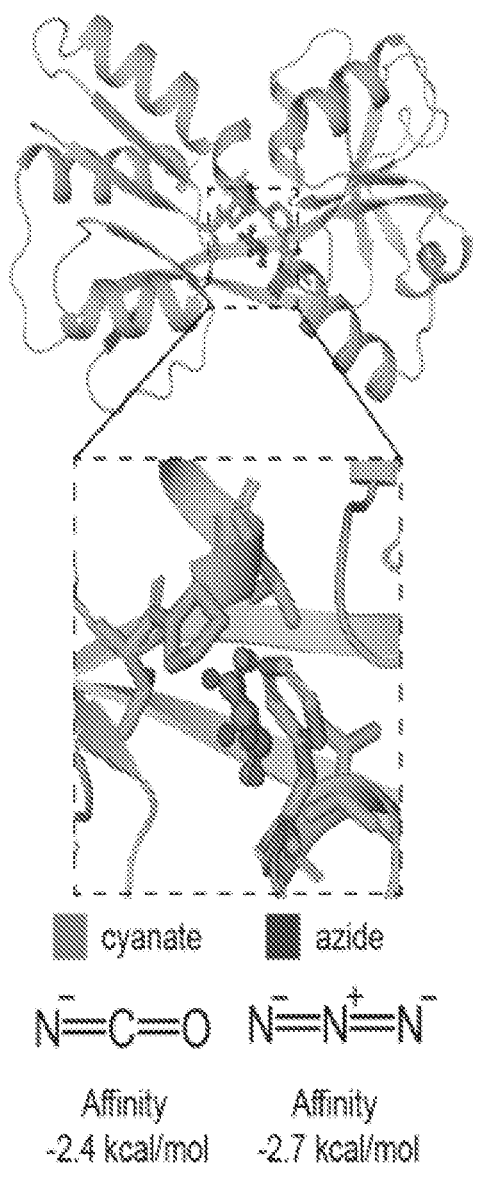

Along with cynTSX genes, the cynR gene encoding cynR protein is present as a part of cyn operon on the opposite strand. Cyanate is a linear small molecule, which binds strongly in the binding pocket of the cynR inducer binding domain. Azide ion is structurally homologous with cyanate and can function as an inducer for the cyn operon. To determine if azide can bind efficiently to cynR, Autodock vina was used to perform docking simulations of both cyanate and azide in the binding pocket of cynR. The binding orientation of docked ligands at minimum free energy reveal a good overlap in the binding site with similar predicted binding affinities (FIG. 1B).

Constructs

The disclosure provides a construct comprising a cyn promoter comprising a consensus ribosome-binding site (RBS) and an engineered −10 sequence and a cynR promoter comprising an engineered −10 sequence. In some embodiments, the engineered −10 sites comprise at least one insertion, deletion, and/or mutation as compared to the naturally-occurring promoter sequences. In some embodiments, the −10 site comprises a consensus sequence. Modifications to the −10 site serve to increase RNA polymerase binding for more efficient transcription. In some embodiments, the ribosome binding site is a consensus sequence that enables efficient ribosome binding and protein translation.

```
pCyn-V2-GFP Cyn promoter
                                              (SEQ ID NO: 36)
TCGCAACCTATAAGTAAATCCAATGGAACTCGTCAGAAATGAGACTTTTACCTTA

TGACAATCGGC TGGTATAAT GCCTCTACTTCCAGAGACAGACATAAGGAGATTA

CGCATG
pCyn-V2-GFP CynR promoter
                                              (SEQ ID NO: 37)
TAGACAGCTGCATGCATCTT TGTTATGGT GTGTTCATATGATAACGGTAATGAGG AACCATG
pCyn-V8-GFP Cyn promoter
                                              (SEQ ID NO: 38)
TCGCAACCTATAAGTAAATCCAATGGAACTCGTCAGAAATGAGACTTTTACCTTA

TGACAATCGGC TGGTATAAT GCCTCTACTTCCAGAGACAGACATAAGGAGATTA

CGCATG
pCyn-V8-GFP CynR promoter
                                              (SEQ ID NO: 39)
TAGACAGCTGCATGCATCTTCCT TATGGT GTGTTCATATGATAACGGTAATGAGG

AACTCTCCATG

Legend:
Sequence with border - -10 site
Bold - Mutational changes
Bold, italic - Additions
Doubly underlined - Ribosomal binding site (SD sequence)
```

In certain embodiments, the construct comprises a nucleic acid sequence selected from the group consisting of SEQ ID NOs. 2-8.

In certain embodiments, the cyn promoter and the independent constitutive promoter are separated by a spacer comprising about 100 to about 1000 nucleotides. In certain embodiments, the cyn promoter and the independent constitutive promoter are separated by a spacer comprising about 10, 20, 30, 40, 50, 60, 70, 80, 90, 100, 200, 300, 400, 500, 600, 700, 800, 900, or 1000 nucleotides.

In certain other embodiments, the cyn promoter and the independent constitutive promoter are not separated by nucleotide spacer (i.e., are directly fused). In certain embodiments, the construct comprises a nucleic acid having the nucleic acid of SEQ ID NO. 1.

In certain embodiments, the constitutive cynR promoter is further engineered to regulate the expression of CynR protein.

In certain embodiments, the disclosure provides a plasmid comprising the construct described elsewhere herein. In certain embodiments, the plasmid comprises an antibiotic resistance gene. In certain embodiment, the antibiotic resistance gene is an ampicillin resistance gene.

In certain embodiments, the plasmid further comprises a gene encoding a protein of interest. In certain embodiments, the gene encoding the protein of interest is located downstream of the cyn operator or promoter region. In certain embodiments, the protein of interest is a reporter protein. In certain embodiments, the reporter protein is a GFP.

In certain embodiments, the expression of the gene encoding the protein of interest is inducible by an azide or a cyanate. In certain embodiments the azide is an inorganic azide. In certain embodiments, the inorganic azide is $NaN_3$. In certain embodiments, the cyanate is NaOCN.

In certain embodiments, the disclosure provides an inducible protein expression system for enhancing the expression protein of interest, wherein the protein expression system comprises a host cell transformed with the plasmid described elsewhere herein.

In certain embodiments, the host cell is an *E. coli* selected from the group consisting of BW25113, BW25113-sCB1 (ΔcynS), BW25113-sKS3 (ΔcynX), and BW52113-sKS4 (ΔcynTSX).

In certain embodiments, the expression of the protein of interest is enhanced by about 20 to about 180 fold to as compared to the expression system comprising the native promoters. In certain embodiments, the expression of the protein of interest is enhanced by about 20, 30, 40, 50, 60, 70, 80, 90, 100, 110, 120, 130, 140, 150, 160, 170, and about 180 fold to as compared to the expression system comprising the native promoters.

In certain embodiments, the disclosure further provides a tunable synthetic biosensor for in vivo detection of inorganic azide, wherein the biosensor comprises the protein expression system, as described elsewhere herein.

Methods

In certain embodiments, the disclosure provides a method of screening activity and specificity of an enzyme in an enzymatic reaction that generates an azide ion. In certain embodiments, the method comprises contacting the biosensor, described elsewhere herein, wherein the protein of interest is a reporter protein, with the azide generated during the enzymatic reaction; and quantifying a signal generated by the reporter protein.

In certain embodiments, the signal comprises a fluorescence signal. In certain embodiments, intensity of the signal is quantified. In certain embodiments, the quantified signal is positively correlated with the activity and the specificity of the enzyme. In certain embodiments, the enzymes are carbohydrate active enzymes. In certain embodiments, the carbohydrate active enzymes are glycosyl hydrolases and transglycosidases. In certain embodiments, the enzymatic reaction is a glycosynthesis reaction that use at least one of a glycosyl azide and a fucosyl azide as donor sugars.

EXPERIMENTAL EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the present disclosure, and are not to be construed as limiting in any way the remainder of the disclosure.

Materials and Methods:

Bacterial Strain Engineering

All the chemicals, reagents and solvents were purchased from Fisher Scientific and Sigma-Aldrich and used without purification. *E. coli* strain used for cloning was E. cloni® 10G (Lucigen, WI, USA) and for protein expression using lac promoter was BL21-CodonPlus-RIPL [λDE3] (Stratagene, Santa Clara, CA, USA). 2× Phusion high fidelity PCR master mix (0.04 U/μL Phusion DNA polymerase, 400 μM dNTPs, 2× Phusion HF buffer, 3 mM $MgCl_2$) was purchased from Thermo Fisher Scientific (USA) and restriction enzymes were procured from New England BioLabs Inc. (USA). The primers used for site directed mutagenesis (SDM), sequence and ligation independent cloning (SLIC) and sequencing reactions were obtained from Integrated DNA Technologies, Inc (USA). Successfully cloned plasmids were isolated from E. cloni® 10 g cells using IBI Scientific (USA) plasmid extraction kit and the sequence was confirmed through Sanger sequencing performed by Genscript Inc. (NJ, USA). The carbohydrate substrates used in enzyme assays were purchased from Synthose Inc, Canada.

The *E. coli* strains used for protein expression using cyn promoter were constructed using the following protocol and reagents outlined in Datsenko (2000). Strains sCB1 (BW25113 cynS::FRT) and sKS3 (BW25113 cynX::FRT) were constructed by first streaking out the strains JW0331 (BW25113 cynS::Kan) and JW0332 (BW25113 cynX:Kan) respectively from the Keio collection onto LB-agar kanamycin (50 μg/ml) plate. The kanamycin marker was then removed by transforming the individual strains with pCP20, following the protocol outlined in Datsenko 2000, and curing the strain of the plasmid. The final strain was diagnosed by PCR and for loss of kanamycin.

Strain sKS4, BW25113 cynR,cynTSX::FRT, was constructed by first transforming the Keio parent strain, BW25113, with pKD46 and plated onto carbenicillin (100 μg/mL) plates. 5 mL overnights of BW25113+pKD46 in LB+carbenicillin (100 μg/mL) were grown at 30° C. and then back-diluted 1:100 into 50 mL LB+carbenicillin (100 μg/mL)+0.2% L-arabinose. The 50 mL culture was grown to an $OD_{600}$ of 0.8, at 30° C., and cells were washed 4 times with 50 mL of ice-cold water. The final cell pellet was resuspended 1:250 the starting culture volume with fresh water and sat on ice until ready to electroporate. The linear DNA fragment, that was used to knockout the cynR gene and cynTSX operon, was synthesized by amplifying the kanamycin gene (Kan) from pKD4 using primers k1 and k2. The linear DNA fragment was checked by gel electrophoresis for purity and was then cleaned-up and concentrated using Qiagen's PCR clean-up kit, the product was eluted in water. The intermediate strain sKS1 (BW25113 cynR, cynTSX::Kan) was made by mixing 100 ng of linear DNA with 50 μL electrocompetent BW25113+pKD46 cells, shocking immediately with 1.8 kV (with a pulse constant of 5.2 ms), and recovered in 900 μL of SOC at 37° C. for 3 hours. After recovery, cells were spun down at 10,000×g for 2 minutes at room temperature, resuspended to 100 plated everything onto kanamycin (50 μg/mL) plates, and grew at 37° C. overnight. sKS1 was transformed with pCP20 to remove the kanamycin selection marker, following the protocol in Datsenko (2000), making the final strain sKS4 (BW25113 cynR,cynSTX:FRT). sKS4 was diagnosed by loss of kanamycin and PCR.

Design and Construction of pCyn Vectors

The cloning of the plasmid constructs used in this study were performed using Sequence and Ligation-Independent Cloning (SLIC) protocol as outlined elsewhere herein. Briefly, to create the pCyn-v1-GFP, the gene fragment consisting of native cynR and cyn promoter/operator region (gblock1) was custom synthesized from Genscript Inc, USA. The GFP gene fragment was taken from pEC-GFP plasmid. Both the gene fragments were cloned into the parent plasmid, ptrc99a while getting rid of the intrinsic lac promoter using the primers p1-p4 and following the SLIC protocol (Table 1). To generate pCyn-v2-GFP, an optimized promoter region was designed in silico and the corresponding DNA fragment (gblock2) was custom synthesized and pCynv-1-GFP was used as starting DNA with primers used being p5-p8. The spacer region of 100 bp from the pCyn-v2-GFP was removed using primers p9-p10 to get pCyn-v3-GFP while an additional random sequence of 900 bp (gblock3) was added using p11-p14 to generate pCyn-v4-GFP. Further, pCyn-v5-GFP was constructed from pCyn-v2-GFP by site directed mutagenesis of the cynR constitutive promoter using primers p15-p16. In the end, the pCyn-v5-GFP was the parent DNA used to create pCyn-v6-GFP, pCyn-v7-GFP and pCyn-v8-GFP using the primers p17-p18, p19-p20 and p21-p22, respectively. All the constructs were diagnosed using Sanger sequences and the sequencing verified plasmids were preserved at −80° C. and their corresponding transformed *E. coli* cells were stored in 15% glycerol stocks at −80° C.

Induction of pCyn-v1/v2-GFP Expression

The pCyn-GFP plasmid constructs were transformed into BW25113 strains (wt, sCB1) and individual colonies were obtained on LB agar plates supplemented with 100 μg/mL Carbenicillin antibiotic. The transformants were inoculated into 10 mL of LB media with carbenicillin and grown at 37° C. for 16 hrs. The 10 mL of overnight grown culture was transferred to 200 mL of fresh LB media with carbenicillin and incubated at 37° C. until mid-exponential phase (OD 0.4-0.6) was reached. At this point, the 200 mL culture was split into six 25 mL falcon tubes. Two of the tubes were induced with 1 mM sodium azide and two tubes with 1 mM cyanate while the remaining two tubes were used as no induction control. The cultures were placed in the 37° C. shaking incubator and 2 mL of sample for bulk fluorescence measurement and 200 μL of sample for flow cytometer runs were collected at every time point.

Induction of pCyn-v2/v3/v4-GFP Expression

The pCyn-GFP plasmid constructs were transformed into BW25113 strains (wt, sCB1, sKS3, sKS4) and individual colonies were obtained on LB agar plates supplemented with 100 μg/ml Carbenicillin antibiotic. The transformants were inoculated into 10 mL of LB media with carbenicillin and grown at 37° C. for 16 hrs. The 10 mL of overnight grown culture was transferred to 200 mL of fresh LB media with carbenicillin and incubated at 37° C. until mid-exponential phase (OD 0.4-0.6) was reached. At this point, the 200 mL culture was split into six 25 mL falcon tubes. Three of the tubes were induced with 1 mM sodium azide and remaining three tubes were used as no induction control. The cultures were placed in the 37° C. shaking incubator and 2 mL of sample was collected at every time point for bulk fluorescence measurement and 200 μL was sampled to measure OD600.

Induction of pCyn-v2/v5/v6/v7/v8-GFP Expression

The pCyn-GFP plasmid constructs were transformed into BW25113 strains (wt, sCB1, sKS3, sKS4) and individual colonies were obtained on LB agar plates supplemented with 100 μg/mL Carbenicillin antibiotic. The transformants were inoculated into 10 mL of LB media with carbenicillin and grown at 37° C. for 16 hrs. Then, 400 μL of overnight grown culture was transferred to 20 mL of fresh LB media with carbenicillin and incubated at 37° C. until an $OD_{600}$ of 0.3-0.4 was reached. At this point, 1 mL of culture was added to 12 wells in a 96 deep well plate. Three wells each were induced with 10 μM, 100 μM 1000 μM of sodium azide and three wells were left uninduced. The 96 well plate was placed in the 37° C. shaking incubator for 2 hours. 200 μL of the sample was used for $OD_{600}$ measurements and the residual sample was used for bulk GFP fluorescence measurement.

Bulk GFP Fluorescence Measurement

The samples collected from each experiment were first centrifuged to remove the LB media. The pelleted cells were resuspended in 250 μL of BPER reagent (Bacterial Protein Extraction Reagent) and incubated at room temperature for 10 min to lyse the cells. The resultant samples were centrifuged and 200 μL of the supernatant was used to measure GFP fluorescence in a black opaque bottom 96 well plate using a spectrophotometer.

Flow Cytometer Data Acquisition and Analysis

For measuring the GFP expression in individual cells, flow cytometer analysis was performed. At each timepoint for a given induction experiment, 200 μL of cells were collected. The cells were centrifuged to remove the LB media components, resuspended in 1× PBS buffer (phosphate buffered saline) and run through the Guava® easyCyte™ flow cytometer to measure the fluorescence distribution at 488 nm excitation and 525 nm emission. The raw data was analyzed using FlowJo software.

Determining if Azide can Bind Efficiently to cynR

To determine if azide can bind efficiently to cynR, Autodock vina was used to perform docking simulations of both cyanate and azide in the binding pocket of cynR. The binding orientation of docked ligands at minimum free energy reveal a good overlap in the binding site with similar predicted binding affinities (FIG. 1B).

Example 1: Improving the Promoter Strength to Enhance the Protein Expression

Figure 1C:
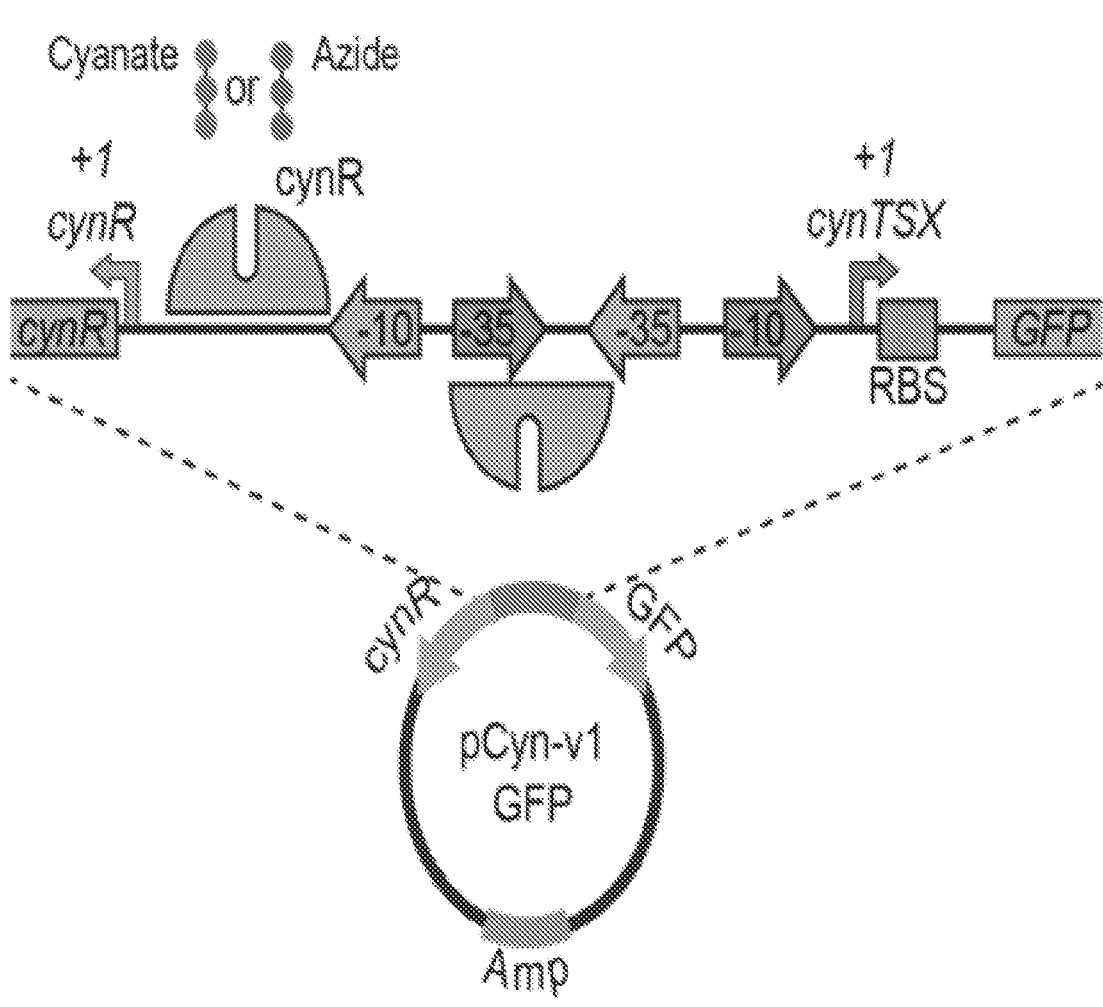
Figure 1D:
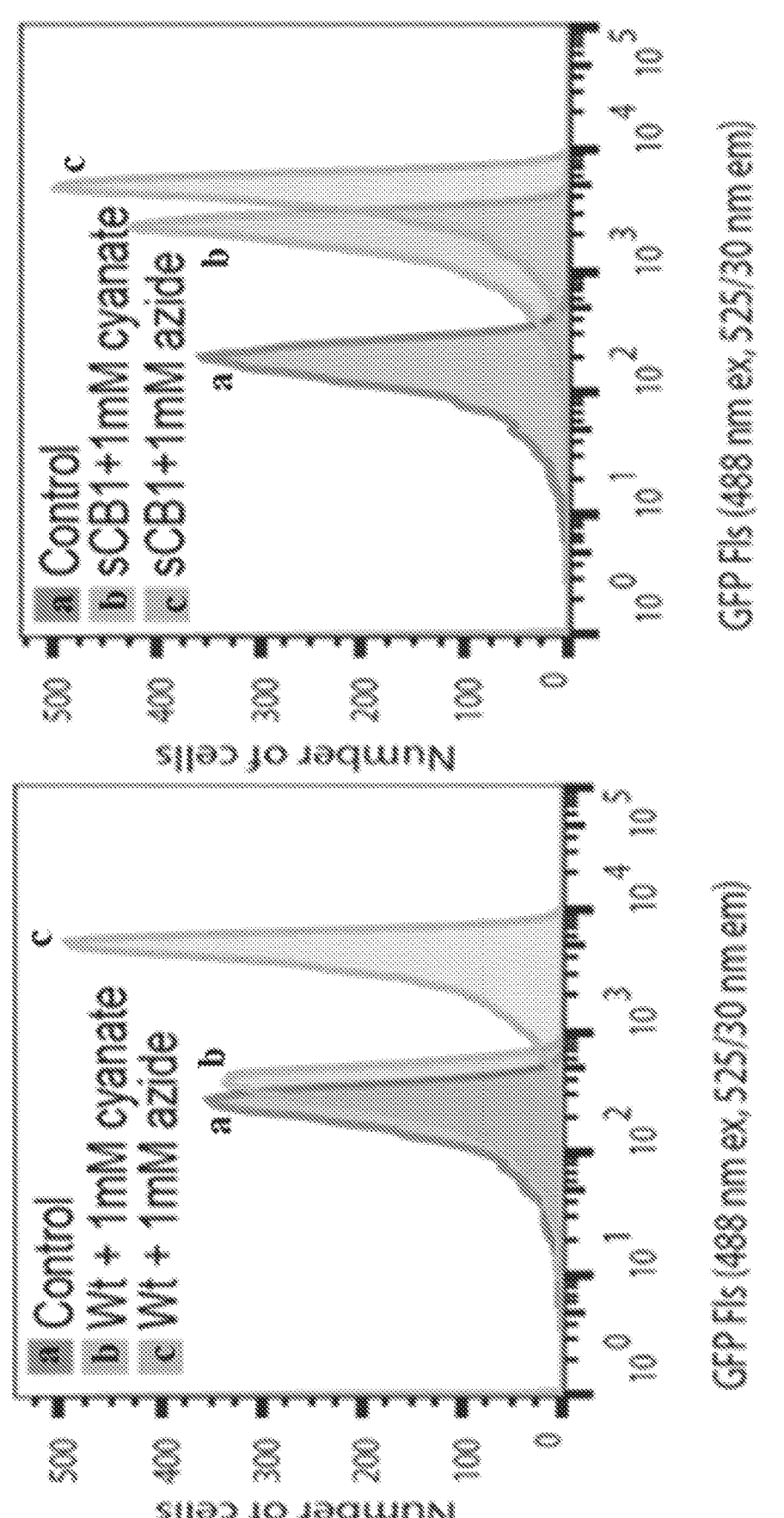
Figure 4:
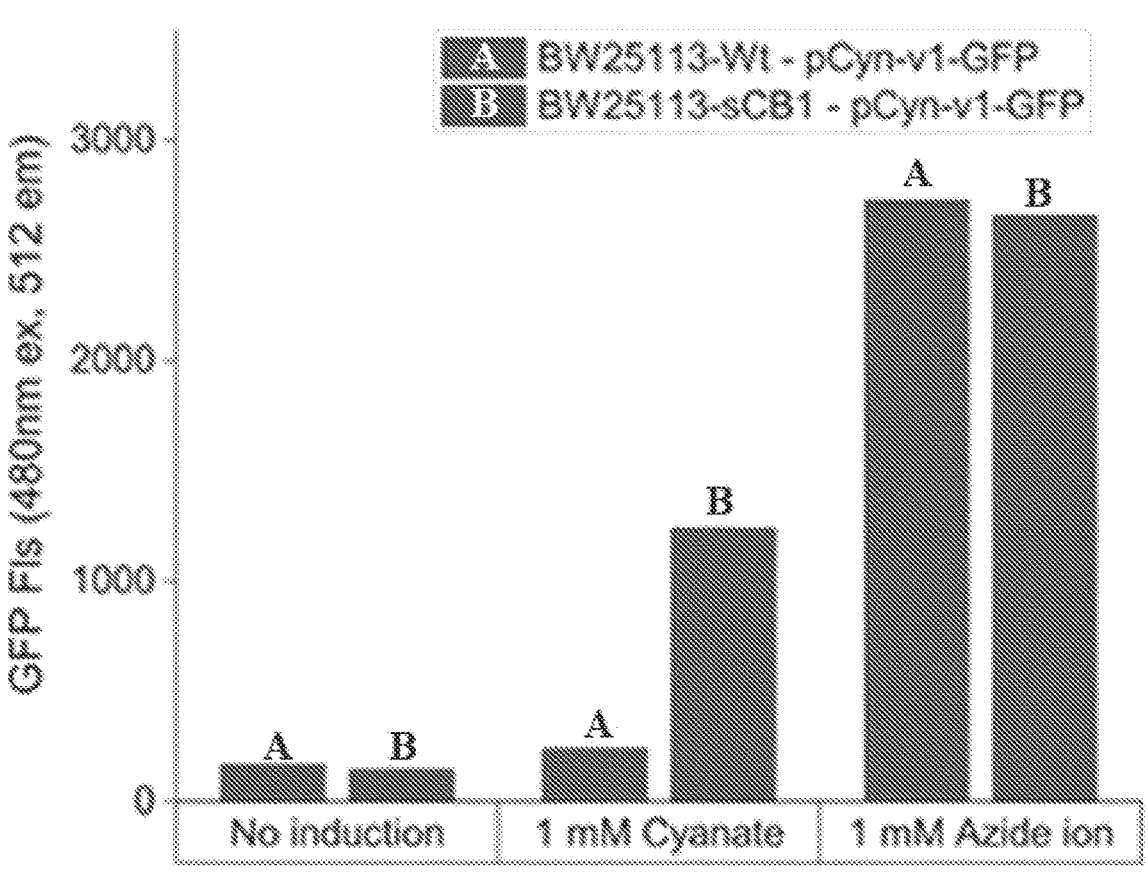
FIG. 4 shows GFP fluorescence of cell lysate after inducing BW25113-Wt and BW25113-sCB1 strains containing pCyn-v1-GFP with cyanate and azide was measured using spectrophotometry.

The regulatory segment consisting of cynR gene and cyn operator region were subcloned into a plasmid vector with ampicillin resistance and a green fluorescent protein (GFP) gene. The regulatory segment was placed upstream of the GFP reporter gene to facilitate GFP expression using cyanate and azide molecules (FIG. 1C). The resultant plasmid (pCyn-v1-GFP) was transformed into *E. coli* BW25113 wildtype strains and induced with 1 mM each of sodium cyanate and sodium azide. The supernatant of lysed cells after induction were used for fluorescence measurements (FIG. 4) and the intact fluorescence of individual cells were analyzed by flow cytometry. FIG. 1D presents the histogram plots of the cells induced for 19 hours. It was observed that as compared to the control (uninduced cells), the azide induced cells had an increase in the fluorescence while the cyanate induction did not result in any GFP expression. Without wishing to be bound by theory, the absence of GFP expression in cyanate induced cells could be due to the breakdown of cyanate by the endogenous cyanate hydratase enzyme in the *E. coli* cells. Hence, the induction capacity of the synthetic promoter was tested in a ΔcynS strain (BW25113-sCB1), which recovered the GFP expression in cyanate induced samples. However, the total amount of protein expressed as estimated by the bulk GFP fluorescence measurements was very low, indicating the poor promoter strength of the native promoter. This is not a surprising result since the native promoter regulates the enzyme expression required to overcome the cyanate toxicity that seldom requires high protein yields. The native operator region contains suboptimal −10 sequence and Shine-Delgarno (SD) sequences (or ribosomal binding site; RBS) which could play a significant role in poor expression strength.

Figure 2A:
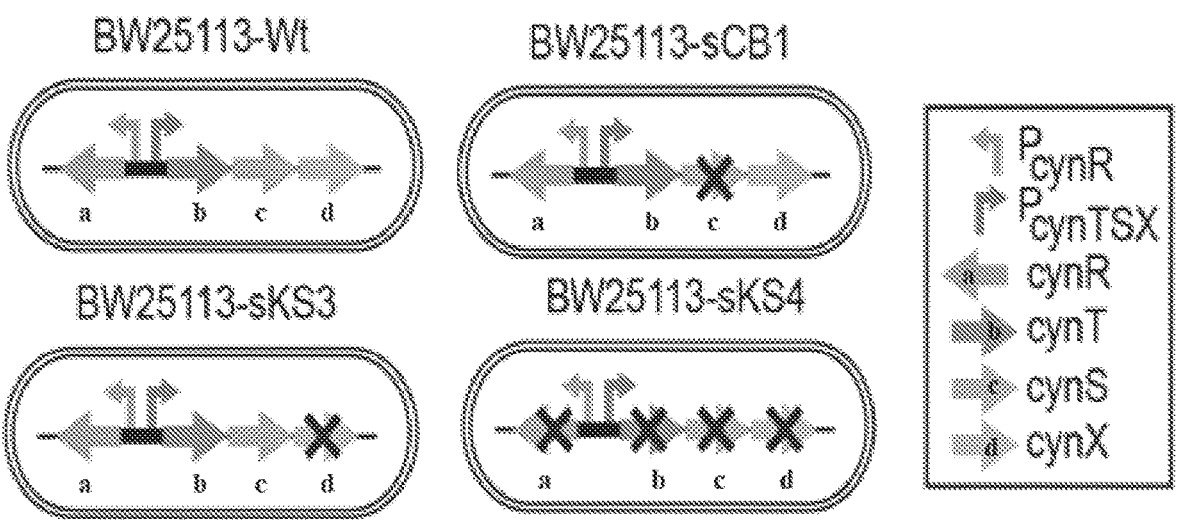
FIGS. 2A-2E illustrate strain engineering and promoter optimization to increase protein expression by azide induction.
Figure 2B:
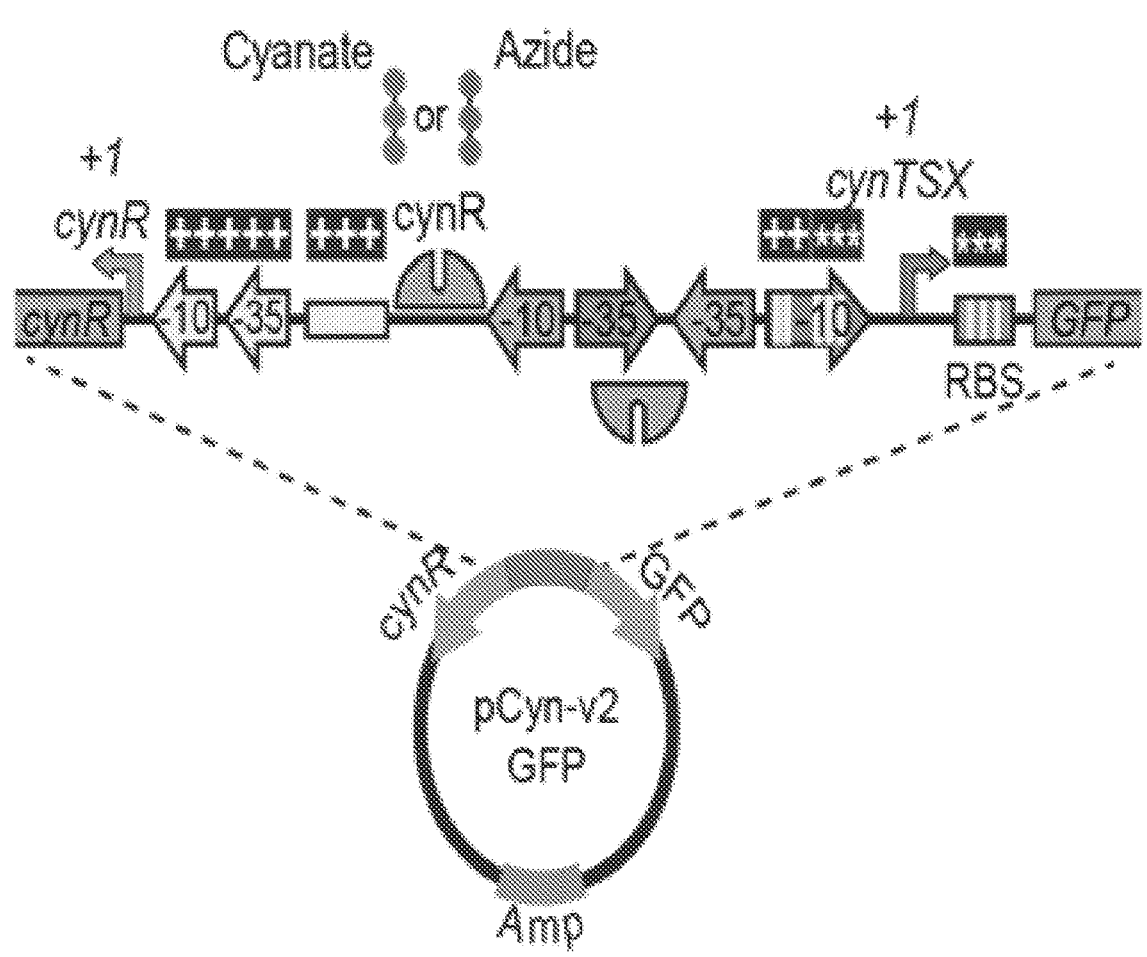
Figure 5A:
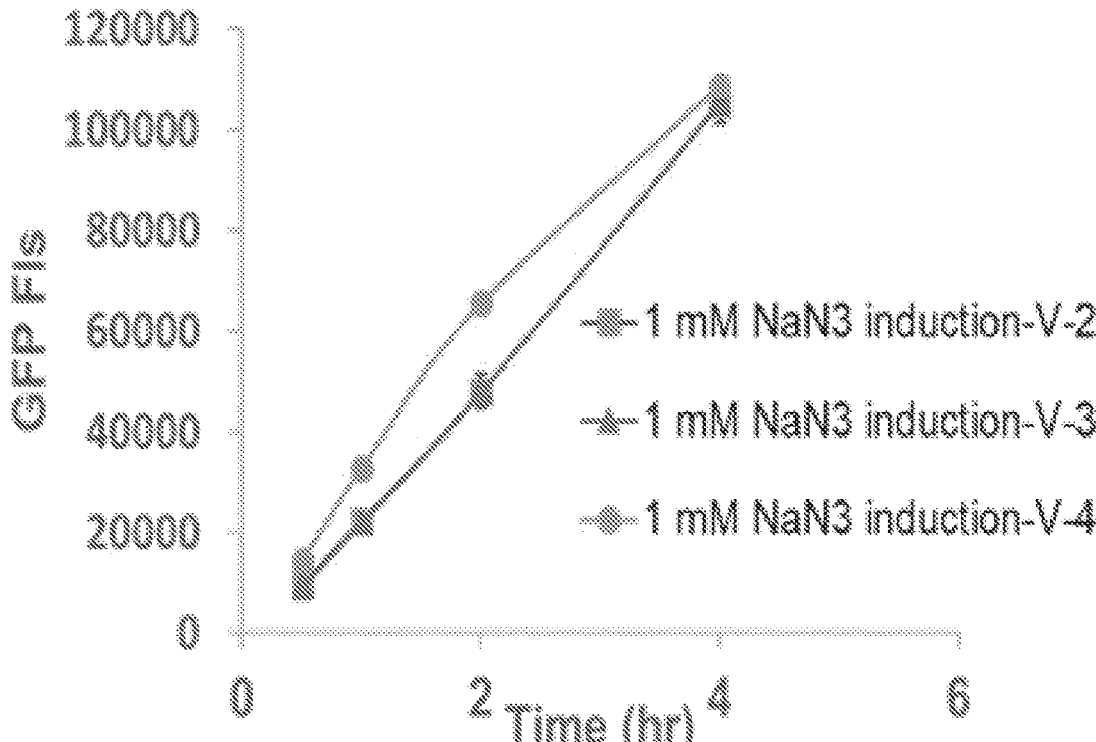
FIGS. 5A-5B illustrate fluorescence measurements of BW25113-Wt cells containing the plasmids pCynv2-GFP, pCyn-v3-GFP and pCyn-v4-GFP and induced with 1 mM sodium azide (FIG. 5A) for 4 hours at 37° C. Uninduced cells are illustrated in (FIG. 5B).
Figure 5B:
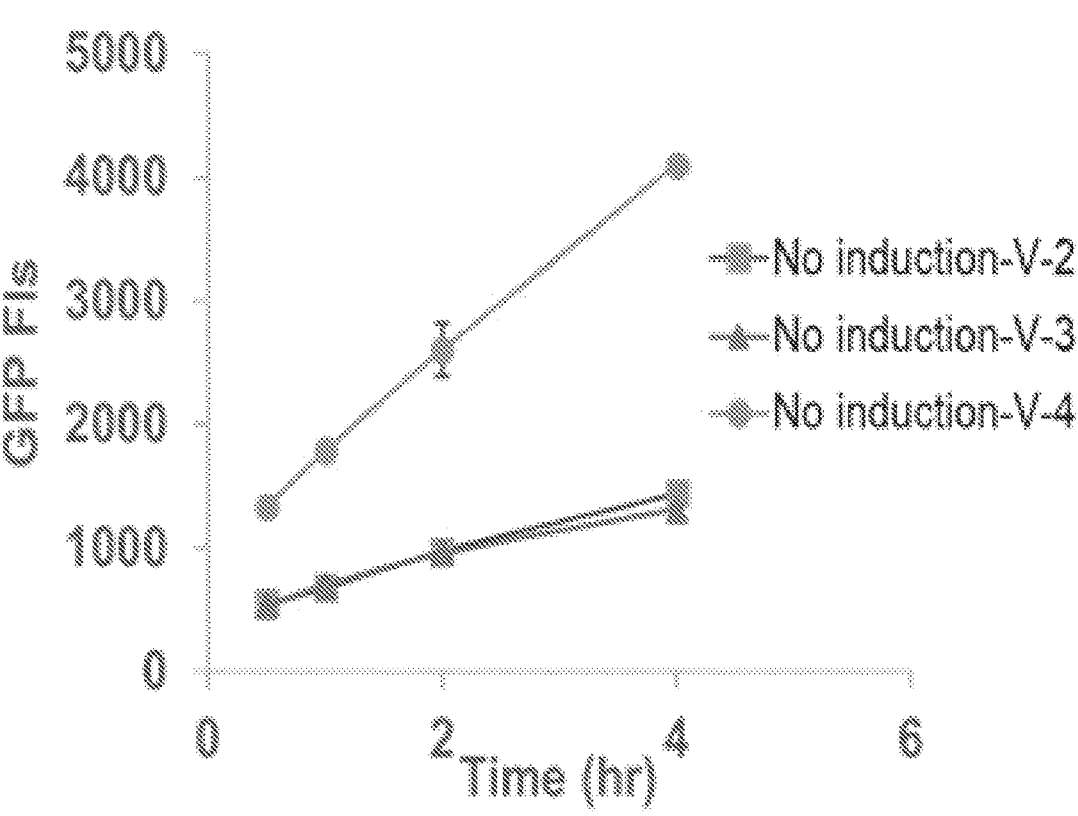

To improve the promoter strength to express high amounts of protein, the native cyn promoter was engineered to contain consensus −10 and SD sequences. The cynR gene which is negatively regulated by cyn promoter was placed under the control of an independent constitutive promoter. Additional to these modifications, to avoid interference and steric hinderances between the two promoters, the promoters were separated by inserting random DNA spacer sequence of 100 bp (pCyn-v2-GFP) and 1000 bp (pCyn-v4-GFP) (FIG. 2B, FIG. 5B). The control construct that contains no spacer sequence (pCyn-v3-GFP) was also generated (FIG. 5A). The modified constructs were individually transformed into the *E. coli* cells and tested for GFP expression using sodium azide.

Figure 2C:
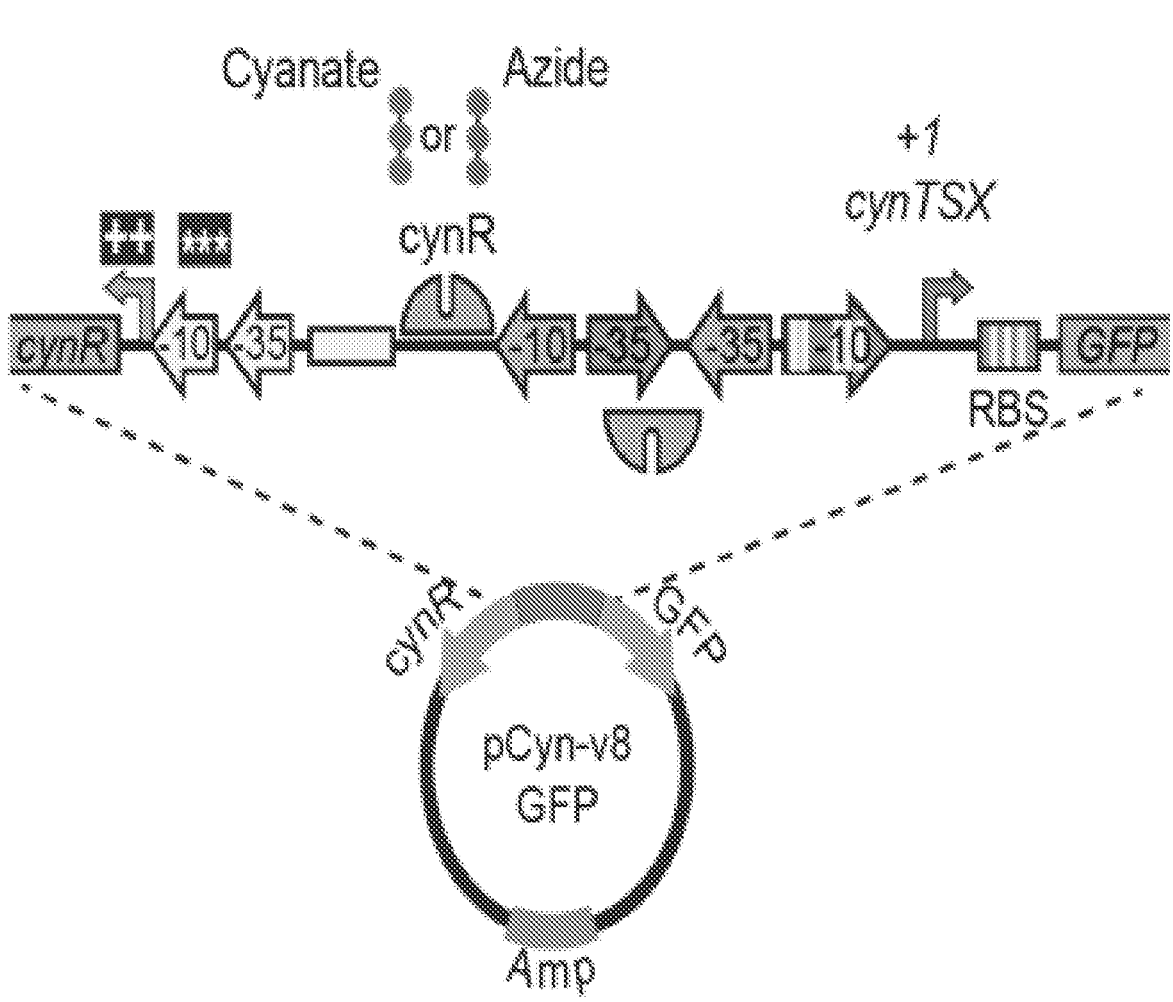
Figure 2D:
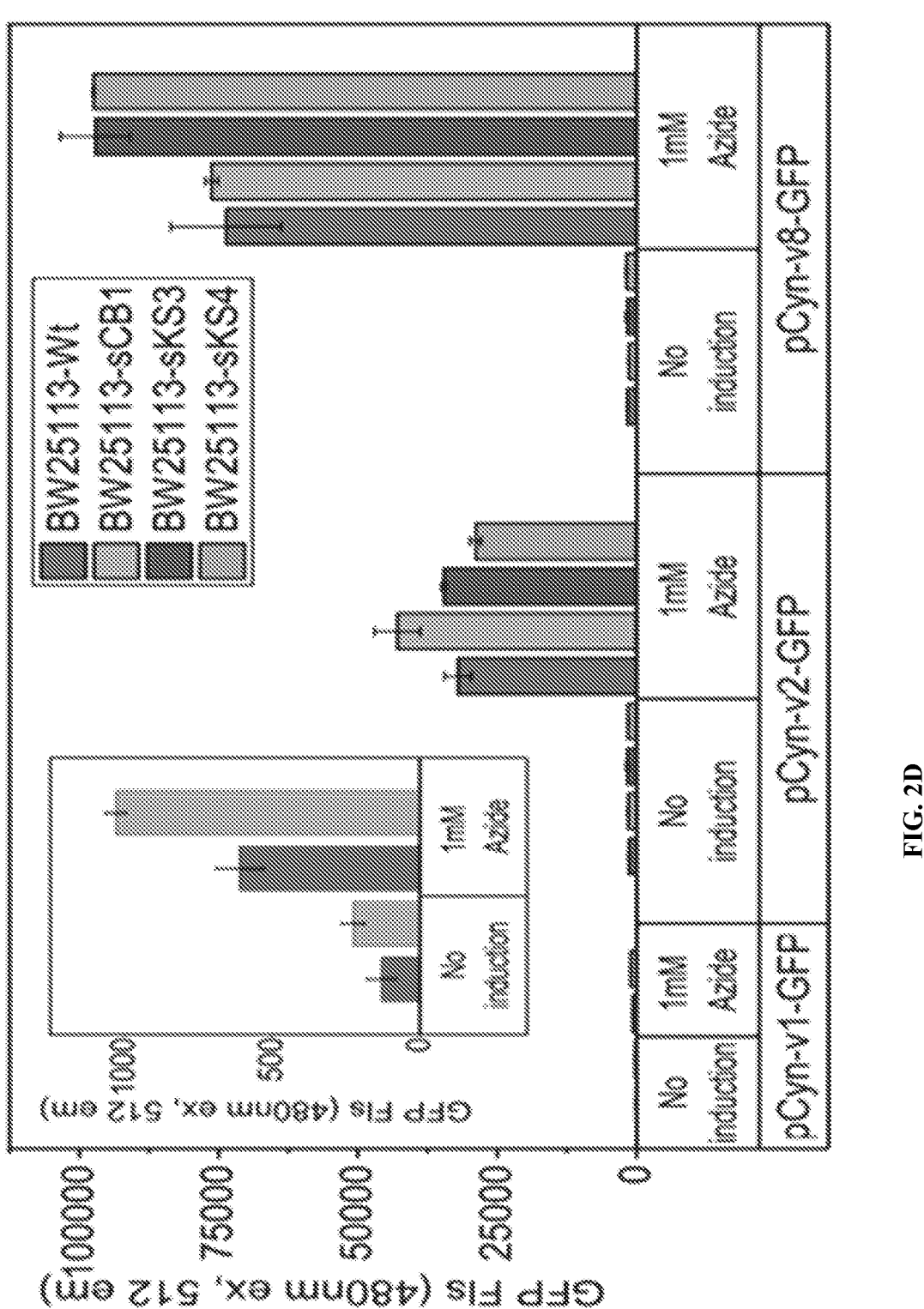

All the three engineered constructs showed a 30-fold increase in the fluorescence signal in the cell lysate, indicating a significant increase in GFP expression as compared to the native promoter (FIG. 2D). The construct with longest spacer region showed around 30% increased fluorescence when compared to no spacer region. However, leaky expression in the v4 (1000 bp) construct was also seen for the no-induction control. The extra sequences could be potentially forming undesirable interactions in the plasmid causing a change in the DNA bending properties.

The promoter regulation is primarily facilitated by the bending of DNA due to the binding of cynR protein and altering the DNA bending could lead to excess expression. Decreasing the length between the promoters largely reduced the leaky expression under no induction while preserving the improved GFP yield when induced with azide (FIGS. 5A and 5B). For all subsequent studies, pCyn-v2-GFP was chosen to keep the promoters isolated from each other.

Figure 2E:
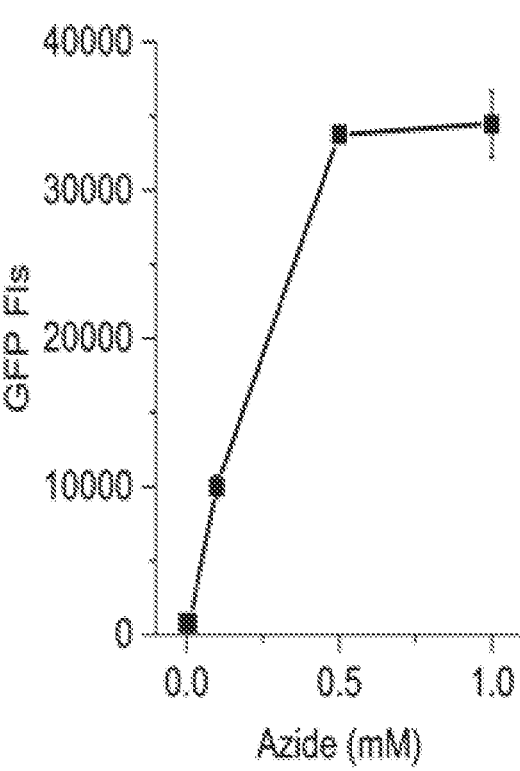
Figure 6:
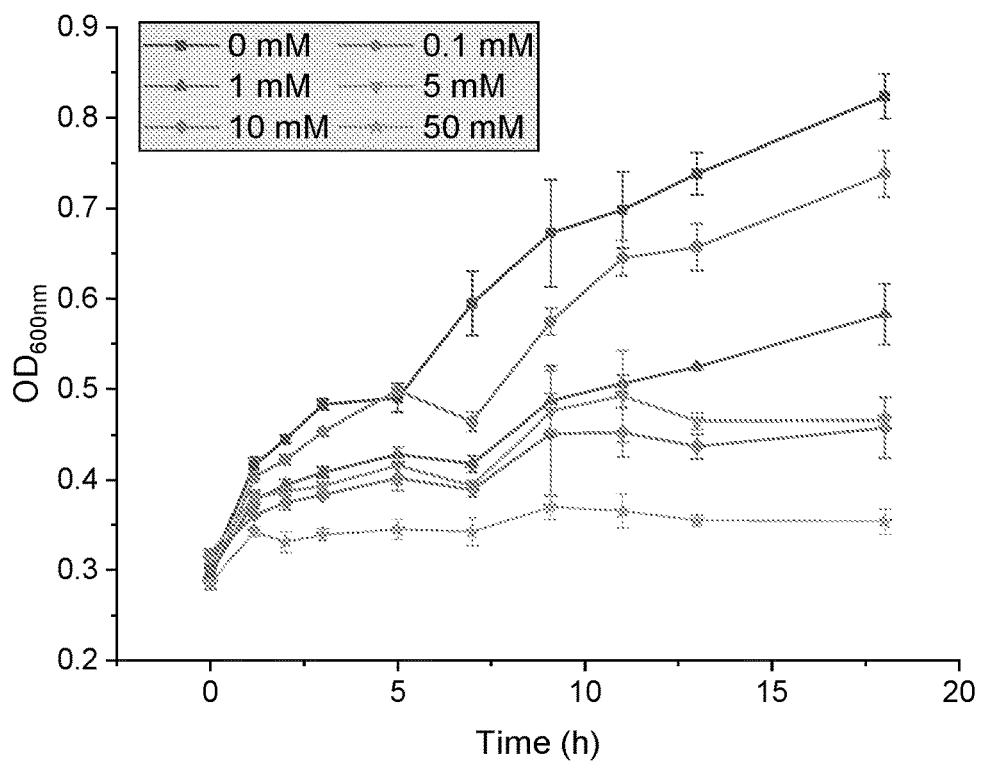
FIG. 6 shows E. coli cells incubated with varying concentrations of sodium azide to study the inhibitory effect of azide on cell growth. Cells were grown in LB media at 37° C. for 18 hours and the OD$_{600}$ of the cells were measured at various time points.
Figure 7:
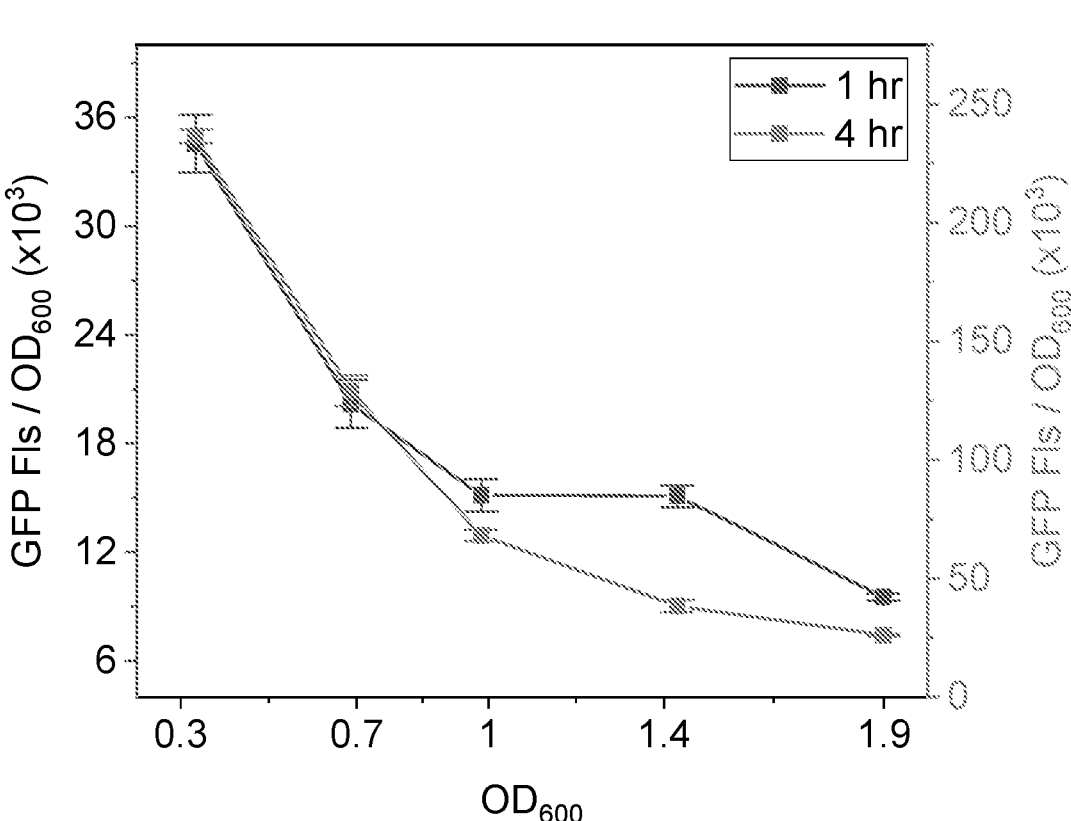
FIG. 7 illustrates GFP fluorescence of the cells induced with 1 mM sodium azide at different starting OD$_{600}$ values. Cells were grown until the desired OD in LB media and induced with 1 mM sodium azide and grown for 4 hours with measurements taken at 1 hour and 4 hours, respectively. The GFP fluorescence on the y-axis is normalized with the measurement OD after induction for specified times.

The 30-fold increase in GFP fluorescence observed was promising to with regard to the pCyn-v2-GFP engineered design for sensing azide inside the cells. To determine the minimal azide amount required to induce protein expression, the cells containing the pCyn-v2-GFP plasmid were induced with varying concentrations of azide. The maximum amount of azide used for induction was limited to 5 mM, as higher amounts show dramatic influence on the growth of the cells (FIG. 6). The bulk GFP fluorescence measurements of cell lysate showed a good correlation of protein expression to the inducer dosage. The GFP expression increased until 1 mM azide induction after which there was reduction in the GFP signal for 5 mM inducer probably due to the toxic effect on cells (FIG. 2E). The lowest tested azide concentration (10 µM) showed a very marginal GFP expression indicating that detection limit for this synthetic promoter would be >10 µM. The bacterial growth phase during the time of induction also play an important role and it was observed that induction at early exponential phase can yield high protein amounts (FIG. 7).

Figure 8:
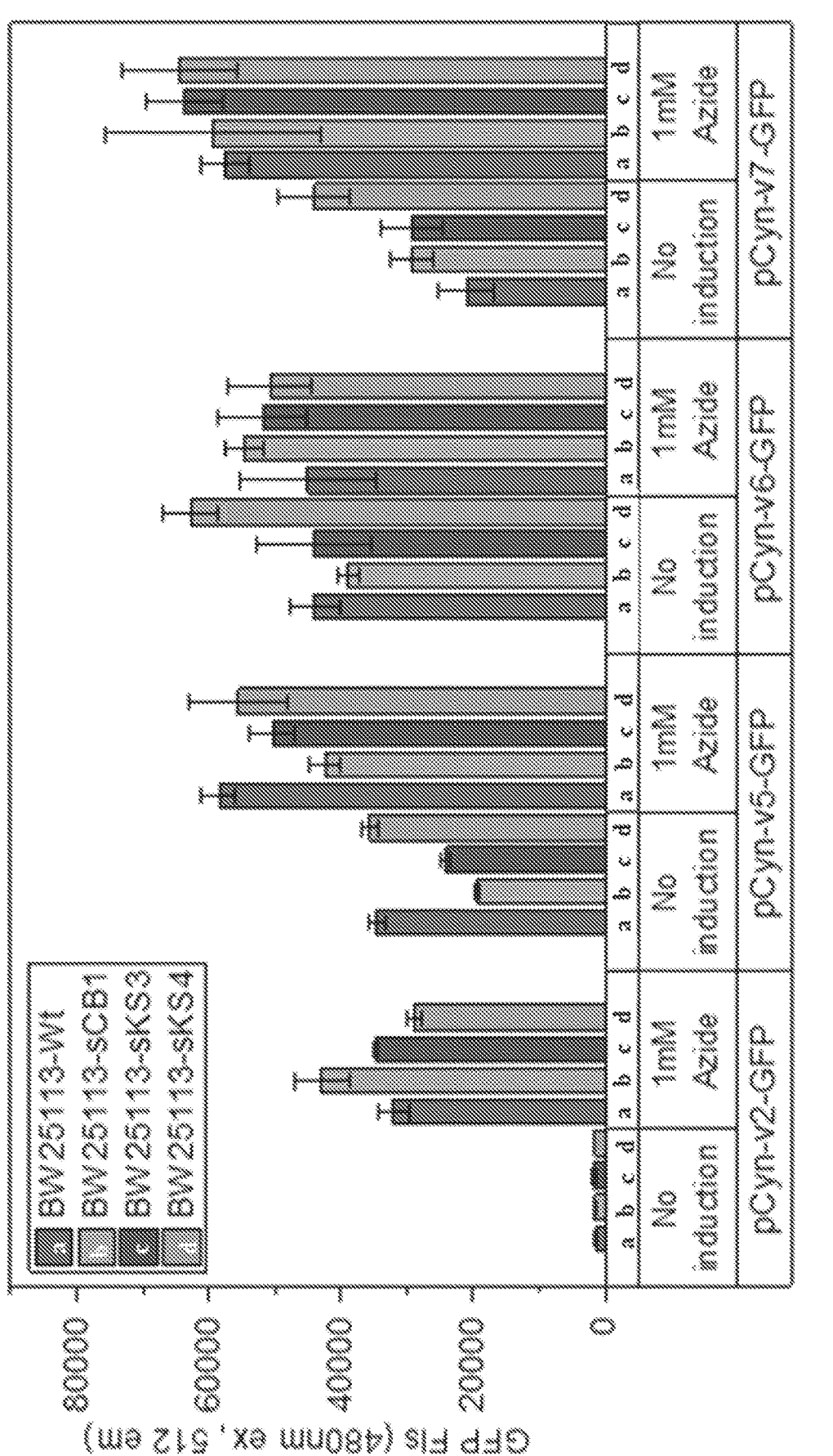
FIG. 8 illustrate fluorescence measurements of BW25113-Wt cells with plasmids pCyn-v2-GFP, pCyn-v5-GFP, pCyn-v6-GFP, pCyn-v7-GFP incubated with 1 mM sodium azide for 2 hours. The fluorescence and OD measurements were taken after 2 hours of induction. The GFP fluorescence was normalized with the OD and plotted as bar graph.

CynR protein acts as a repressor for the promoter by causing a bend at −35 site hindering the binding of RNA polymerase. The cynR protein consists of two domains: an inducer binding domain and a DNA binding domain. The inducer binding domain binds to the inducer (cyanate or azide), which decreases the bend at promoter site to facilitate transcription. In regulating protein expression, along with the inducer amount, the relative amounts of cynR protein is also critical. The cynR constitutive promoter was further engineered to adjust the repressor protein expressed. Four different constructs (v5, v6, v7 and v8) were constructed by creating mutations at the −10 site, regions between −10 and −35 site and between RBS and translation start site (TSS) (FIG. 2C). The expression strength of these modified promoters was tested in wild type (BW25113) and different knockout strains (sCB1, sKS3, sKS4) using GFP fluorescence. The pCyn-v8-GFP construct which had reduced efficiency at −10 site but optimal length of 8 nucleotides between RBS and TSS gave a 120 to 160 fold increase in the fluorescence as compared to native promoter with the maximum fold increase observed in ΔcynX (sKS3) and ΔcynR, ΔcynTSX (sKS4) knockout strains (FIG. 2D). On the other hand, the designs (v5, v6, v7) not only did not show any significant increase in fluorescence with respect to v2 design, but also impacted the leaky expression when no inducer added (FIG. 8).

Figure 9:
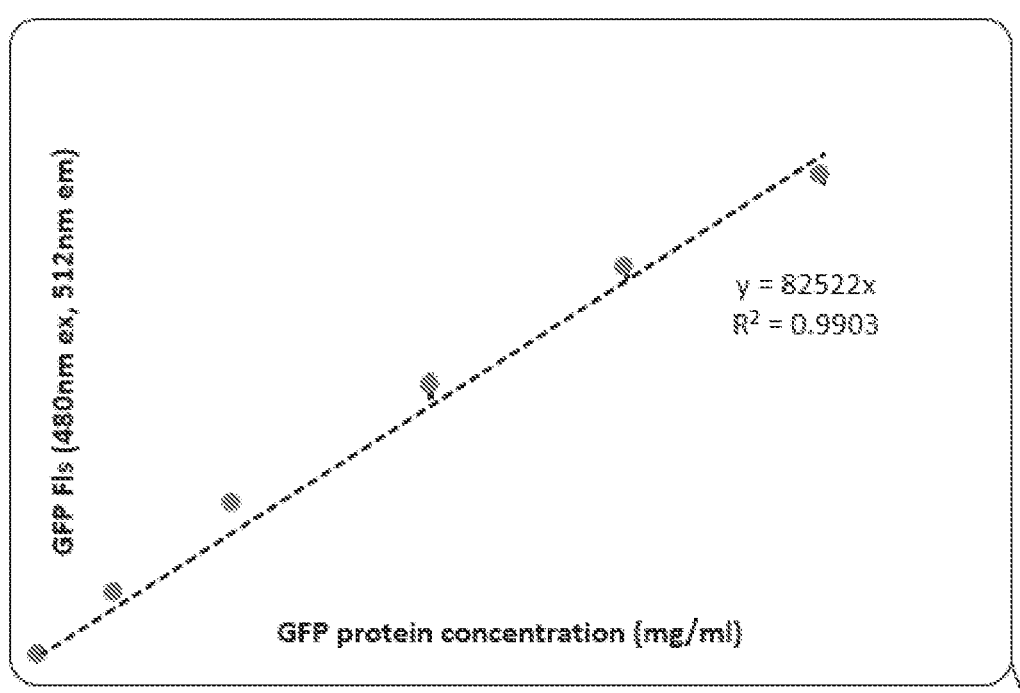
FIG. 9 is a calibration curve for GFP protein concentration (mg/mL) and fluorescence measurements.

The optimized designs (pCyn-v2-GFP and pCyn-v8-GFP) function as a tunable synthetic biosensor for in vivo detection of azide. The amount of GFP expressed within 2 hours of 1 mM azide induction in BW25113-Wt strain was estimated to be 0.4 mg and 0.9 mg from 1 mL culture for pCyn-v2-GFP and pCyn-v8-GFP, respectively based on calibration curve between protein concentration and GFP fluorescence (FIG. 9). The protein expression efficiency of the engineered promoter (pCyn-v2-GFP) was compared against the engineered lac expression system.

Figure 3A:
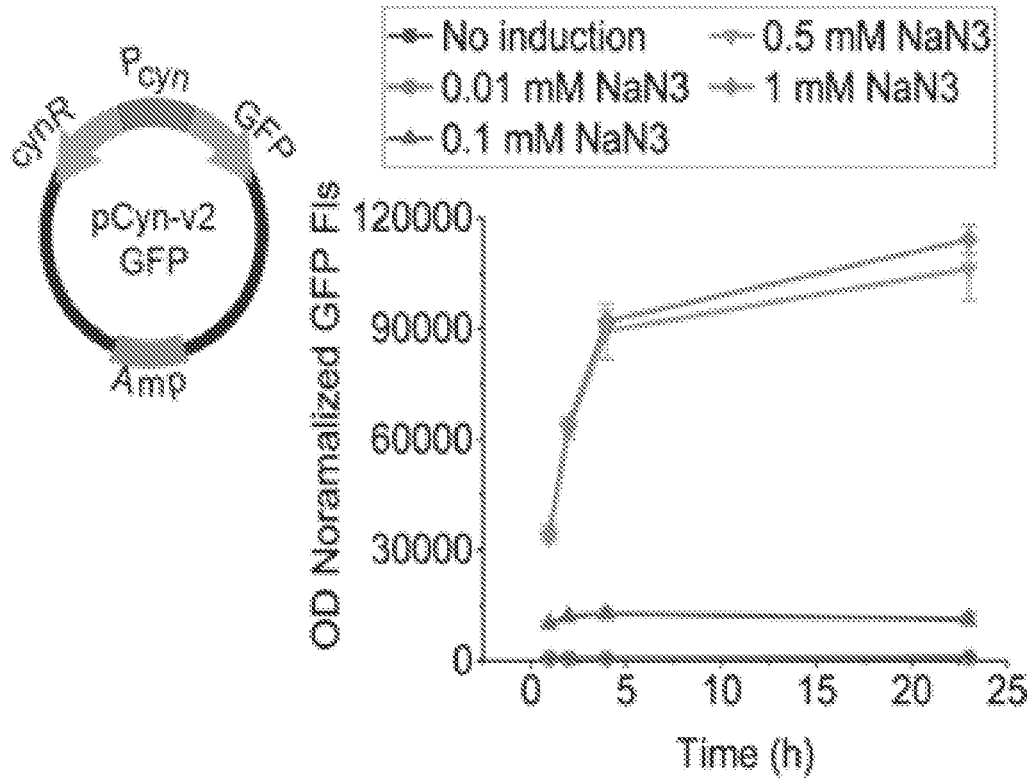
FIGS. 3A-3C illustrate that the synthetic promoter shows application towards protein expression and chemical biology.
Figure 3B:
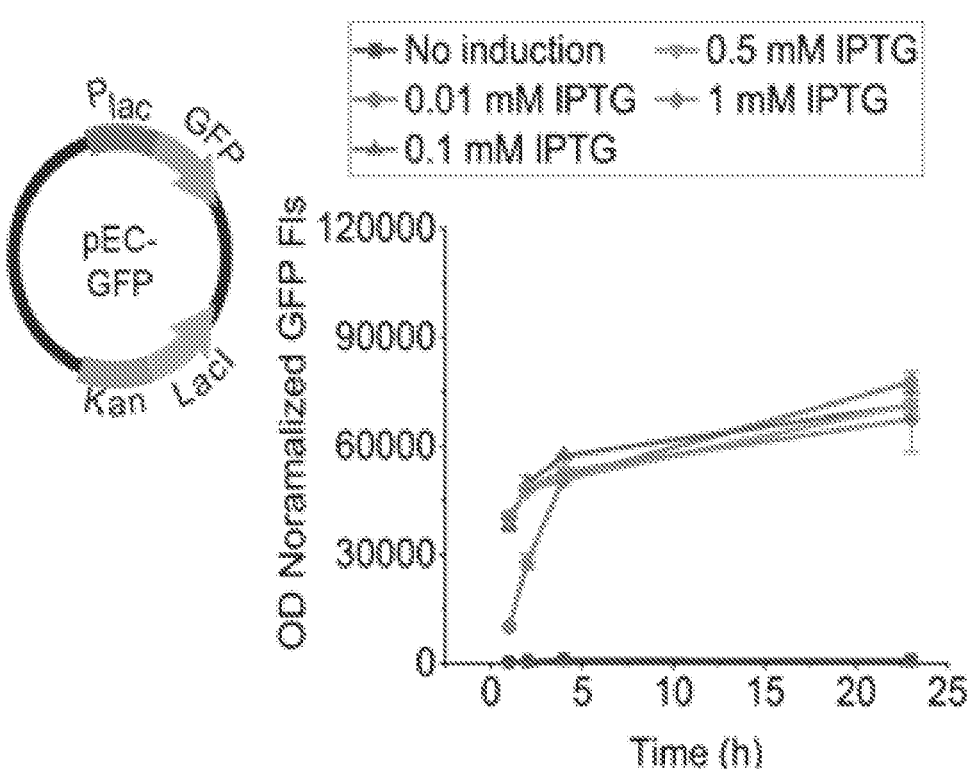

The synthetic cyn promoter in BW25113-Wt (FIG. 3A) and lac promoter in BL21 cells (FIG. 3B) were induced using sodium azide and IPTG respectively at various concentrations between 0.01 mM to 1 mM. The amount of protein expressed in Pin system was higher during in the early time points after induction and at low inducer concentrations. Even at lower IPTG concentrations (0.01 mM and 0.1 mM), GFP expression increased with time and reached maximum after 24 hours of induction, whereas a relatively lower (or no) GFP expression at similar azide concentrations were seen (FIGS. 3A-3B). However, a tunable expression using azide induction was observed, as GFP expression was found to be proportional to inducer concentration. Also, the maximum GFP expression achieved after 24 hours was much higher for cyn promoter than lac promoter at higher inducer concentrations (>0.5 mM) (FIGS. 3A-3B). These results present the utility of the plasmid harboring optimized $P_{cyn}$ promoter as an alternative expression vector.

Example 2: Use as an Azide Biosensor

In addition to functioning as an expression system, the developed promoter can prove to be useful in chemical biology especially for enzyme engineering. This method is a powerful tool to selectively identify inorganic azide amongst other chemically linked azides. Enzymatic reactions which result in the release of azide ions can be identified using this promoter. Carbohydrate active enzymes involving glycosyl hydrolases and transglycosidases are such enzymes that have been shown to release azide from azido-sugars for hydrolysis and carbohydrate synthesis. Multiple glycosyl azides such as galactosyl-, glucosyl- and mannosyl-azides were hydrolyzed by galactosidases, glucosidases, and mannosidases respectively. Similarly, engineered glycosidases (e.g., transglycosidases and glycosynthases) used these azido-hexoses and their N-acetyl derivatives as donor sugars for oligosaccharides synthesis. β-glucosidases from *Aspergillus* sp., and *Agrobacterium* sp. belonging to glycosyl hydrolase family GH3 and GH1 actively cleaved azide group from glucosyl azide. Two β-glucosidases from the GH1 and GH3 families are present in *E. coli* which can potentially show similar substrate specificity to release azide when incubated with glucosyl azide.

Figure 3C:
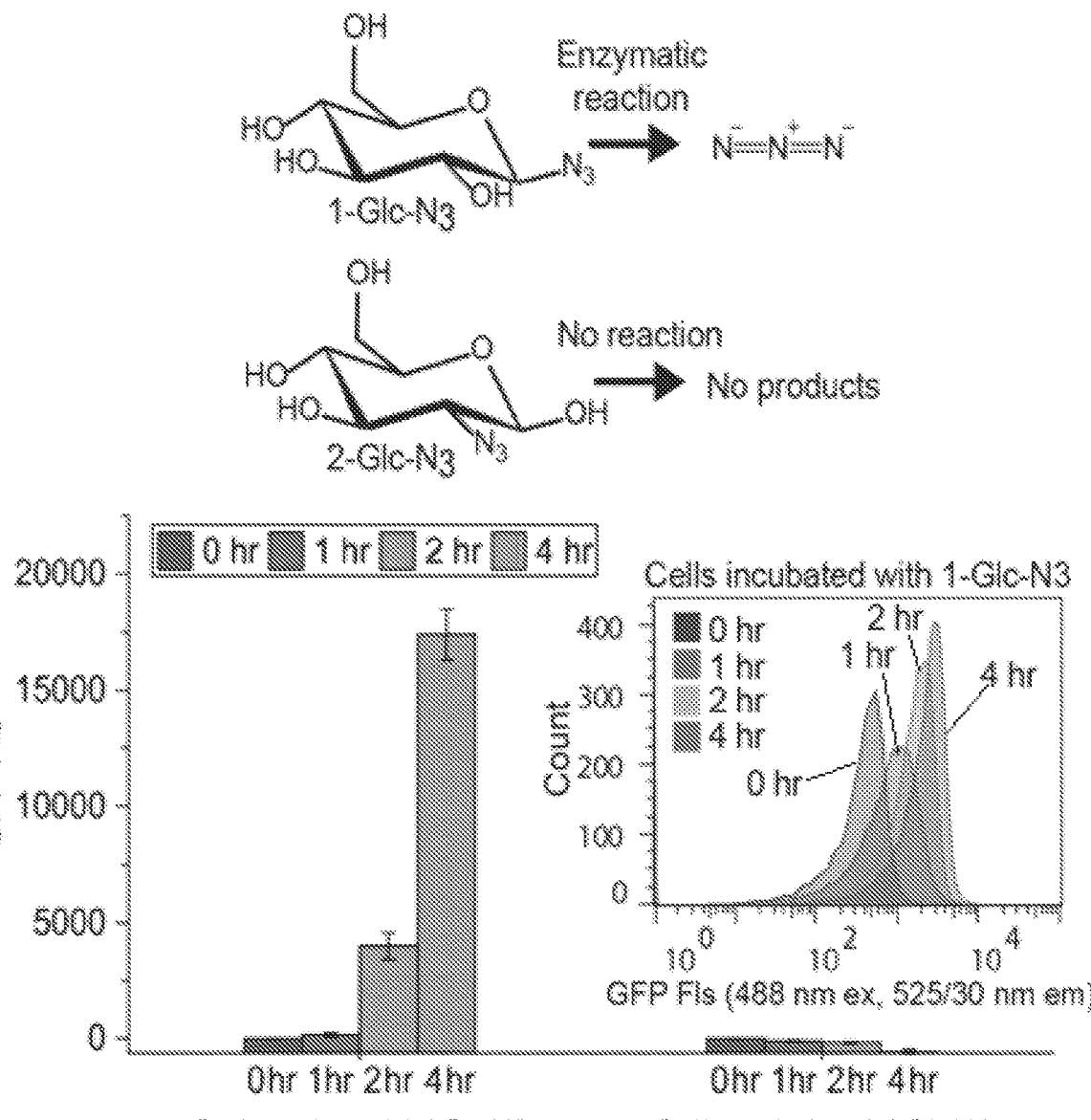

Here, *E. coli* BW25113-Wt cells containing the engineered pCyn-v2-GFP plasmid were incubated with 1-azido-β-D-glucopyranosyl azide (1-Glc-$N_3$) for 4 hours. As illustrated in FIG. 3C, a small change in GFP fluorescence was observed in the first hour after which a rapid increase in fluorescence was observed owing to the release of azide for 1-Glc-$N_3$. To verify if the detected GFP fluorescence is due to cleavage of azide and not due to azido-glucose, the cells were incubated with 2-Deoxy-2-azido-β-D-glucopyranosyl azide (2-Glc-$N_3$). No change in fluorescence was detected in the control samples since 2-Glc-$N_3$ is not hydrolyzed by β-glucosidases and hence cannot release free azide for induction of the promoter. This preferential sensitivity of the designed promoter towards azide ions can be used for in vivo engineering of efficient enzymes for sugar polymer synthesis and hydrolysis.

Example 3: Glycosynthase Enzyme Engineering and Screening Using Flow Cytometry

Figure 10A:
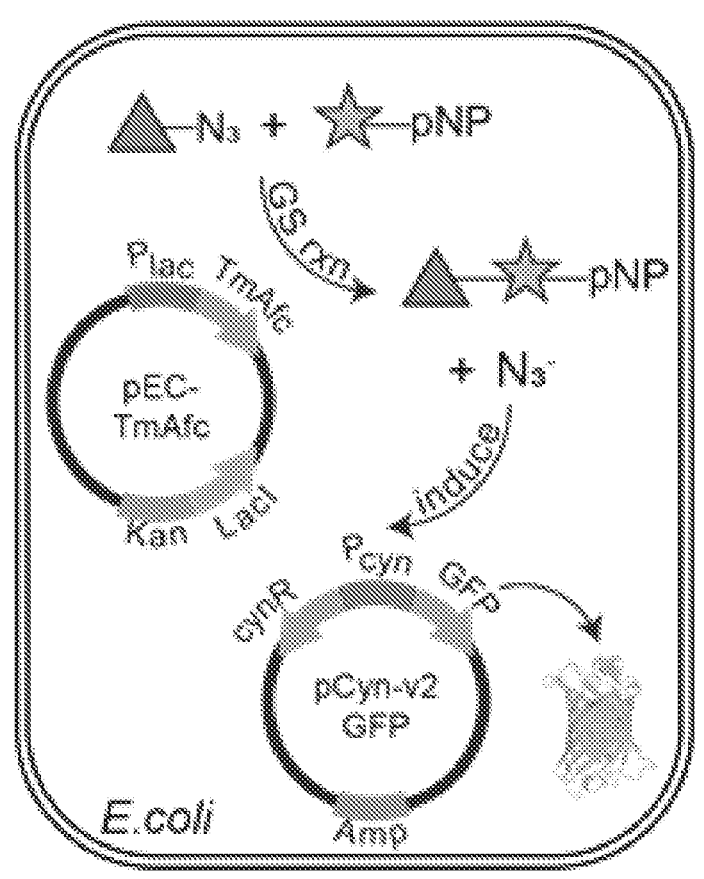
FIGS. 10A-10B illustrates that glycosynthase enzyme engineering and screening using flow cytometry is enabled using an azide promoter system.

*E. coli* containing two plasmids, pEC-TmAFc and pCyn-v2-GFP, comprising lac and cyn promoters, respectively, were incubated with glycosynthases reaction substrates (e.g., fucosyl azide and pNP-xylose). Induced expression of TmAfc-D224G results in the mutant enzyme, which alone catalyzes the glycosynthase (GS) reaction, thereby generating azide ion as a by-product. The azide ion product further induces the azide promoter on the secondary plasmid (i.e., pCyn-v2-GFP) resulting in GFP expression (FIG. 10A).

Figure 10B:
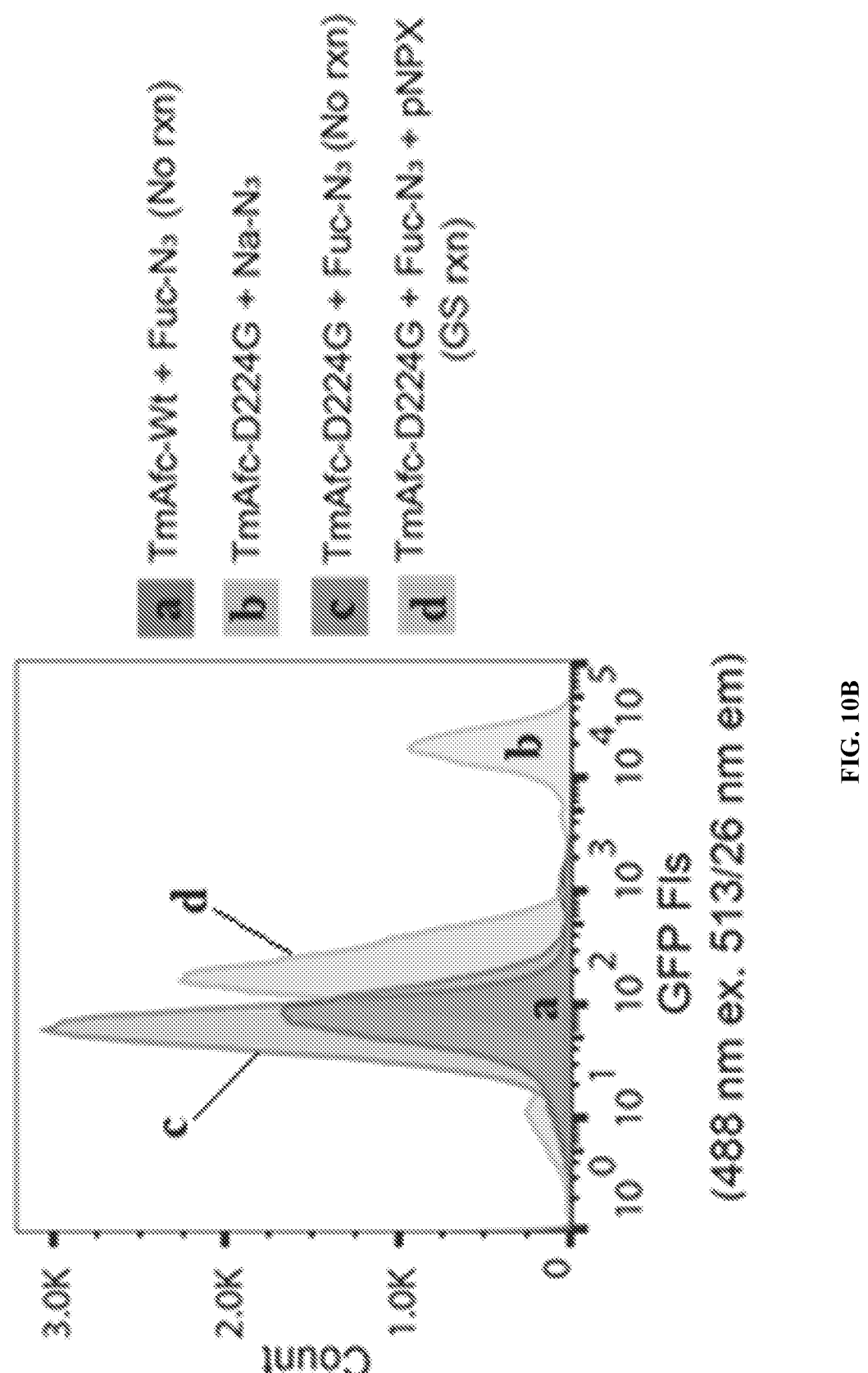

Flow cytometry analysis of *E. coli* cells containing dual plasmids (i.e. pEC-TmAFc and pCyn-v2-GFP) with glycosynthase substrates and various controls to demonstrate the utility of the azide promoter system. It was found that only cells expressing the TmAFc-D224G mutant and in the presence of both GS and reaction donor/acceptor sugar substrates provided a clear shift in cell fluorescence, a result of azide ion release during the GS reaction (FIG. 10B).

```
Sequence Listing
SEQ ID NO. 1: Promoter region for pCyn-v1-GFP
TCGCAACCTATAAGTAAATCCAATGGAACTCATCATAAATGAGACTTTTACCTTATGACAAT

CGGCGAGTAGTCTGCCTCTCATTCCAGAGACAGACAGAGGTTAACGATG

SEQ ID NO. 2: Promoter region for pCyn-v2-GFP
GGTTCCTCATTACCGTTATCATATGAACACACCATAACAAAGATGCATGCAGCTGTCTAAAT

CCCGCGGCCATGGCGGCCGGGAGCATGCGACGTCGGGCCCAATTCGCCCGATCTTAATGAAT

GGCCGGAAGAGGTACGGACGCGATATGCGGGGGTGAGAGGGCAAATAGGCAGGTTCGCCTTC

GTCACGCTAGGAGGCAATTCTATAAGGATCCTCGCAACCTATAAGTAAATCCAATGGAACTC

GTCAGAAATGAGACTTTTACCTTATGACAATCGGCTGGTATAATGCCTCTACTTCCAGAGAC

AGACATAAGGAGATTACGCATG

SEQ ID NO. 3: Promoter region for pCyn-v3-GFP
GGTTCCTCATTACCGTTATCATATGAACACACCATAACAAAGATGCATGCAGCTGTCTAAAT

CCCGCGGCCATGGCGGCCGGGAGCATGCGACGTCGGGCCCAATTCGGGATCCTCGCAACCTA

TAAGTAAATCCAATGGAACTCGTCAGAAATGAGACTTTTACCTTATGACAATCGGCTGGTAT

AATGCCTCTACTTCCAGAGACAGACATAAGGAGATTACGCATG

SEQ ID NO. 4: Promoter region for pCyn-v4-GFP
GGTTCCTCATTACCGTTATCATATGAACACACCATAACAAAGATGCATGCAGCTGTCTAAAT

CCCGCGGCCATGGCGGCCGGGAGCATGCGACGTCGGGCCCAATTCGCCCGATCTTAATGAAT

GGCCGGAAGAGGTACGGACGCGATATGCGGGGGTGAGAGGGCAAATAGGCAGGTTCGCCTTC

GTCACGCTAGGAGGCAATTCTATAAGATTGGACCGTACGCATGTCAAACTGCTGGCGAACCG

CGATTCCACGACCGGTGCACGATTTAACTACGCCGACGTGACGACATTCCTGCTAATGCCTC
```

-continued

GCCCGCCGGACCGCCCTCGTGATGGGGTAGCTGGGCATGACCTTGTGACATATAACGAGAGT

CTACTTGTTTAATCATCTCACGGCGAAAGTCGGGGGGACAGCAGCCGCTGCAGACATTATAC

CGCAACTACACCAAGCTGAGATAACTCCGTAGTTGACTACGCATCCCTCTAGGCCTTACTTA

ACCGGATACAGTGACTTTGACAGGTTTGTGGGCTACAGCAATCACTTGCATAGCTGCGTATG

GAGGAAGCAACTCTTGGGTGTTAGTATGTTGACCCCTGTATTAGGGATGCGGGTAGTAGATG

TGGGCAGAGACACCCAGGTCAAGTACACGACCCTCTCGTAGGAGGTGTTCCAGATCACCATA

CCACCATACCATTCGAGCATGGCACTATGTACGCTGTCCCCATTCTGGTAGTCATCATCCCT

ATCACGGTTTCGAGTGACTGGTGACGGATATCCCCCACGAATGGAGATCTTATTCACAGTCG

GTCACATTGGAGTGCTCCTTGACTAATCAGCTTGGCCAGGTCTGTTGGGCCTCCGTGCCCCG

AGTTTCGGCGCTGTGCTGCCGAGAGTCGGCCATTGTCATTGGGGCCTCACTTGTGGATACCC

CGACCTATTTTGACGGGACCACTCGCGGTAGTCGTTGGGCTTATGCACCGTGAAGTCCTCCG

CCGGCCTCCCCCCTACAAAAGATGATAAGCTCCGGCAAGCAATATTGAACAACGCAAGGATC

GGCGATATAAACAGAGAAACGGCTGATTACTCTTGTTGGTGTGGTATCGCTAAACTGGGATC

CTCGCAACCTATAAGTAAATCCAATGGAACTCGTCAGAAATGAGACTTTTACCTTATGACAA

TCGGCTGGTATAATGCCTCTACTTCCAGAGACAGACATAAGGAGATTACGCATG

SEQ ID NO. 5: Promoter region for pCyn-v5-GFP
GGTTCCTCATTACCGTTATCATATGAACACACCATAAGGAAGATGCATGCAGCTGTCTAAAT

CCCGCGGCCATGGCGGCCGGGAGCATGCGACGTCGGGCCCAATTCGCCCGATCTTAATGAAT

GGCCGGAAGAGGTACGGACGCGATATGCGGGGGTGAGAGGGCAAATAGGCAGGTTCGCCTTC

GTCACGCTAGGAGGCAATTCTATAAGGATCCTCGCAACCTATAAGTAAATCCAATGGAACTC

GTCAGAAATGAGACTTTTACCTTATGACAATCGGCTGGTATAATGCCTCTACTTCCAGAGAC

AGACATAAGGAGATTACGCATG

SEQ ID NO. 6: Promoter region for pCyn-v6-GFP
GGTTCCTCATTACCGTTATCATATGAACACGCCATAAGGAAGATGCATGCAGCTGTCTAAAT

CCCGCGGCCATGGCGGCCGGGAGCATGCGACGTCGGGCCCAATTCGCCCGATCTTAATGAAT

GGCCGGAAGAGGTACGGACGCGATATGCGGGGGTGAGAGGGCAAATAGGCAGGTTCGCCTTC

GTCACGCTAGGAGGCAATTCTATAAGGATCCTCGCAACCTATAAGTAAATCCAATGGAACTC

GTCAGAAATGAGACTTTTACCTTATGACAATCGGCTGGTATAATGCCTCTACTTCCAGAGAC

AGACATAAGGAGATTACGCATG

SEQ ID NO. 7: Promoter region for pCyn-v7-GFP
GTTCCTCATTACCGTTATCATATGAACACACCATAAGGAAAAGATGCATGCAGCTGTCTAAA

TCCCGCGGCCATGGCGGCCGGGAGCATGCGACGTCGGGCCCAATTCGCCCGATCTTAATGAA

TGGCCGGAAGAGGTACGGACGCGATATGCGGGGGTGAGAGGGCAAATAGGCAGGTTCGCCTT

CGTCACGCTAGGAGGCAATTCTATAAGGATCCTCGCAACCTATAAGTAAATCCAATGGAACT

CGTCAGAAATGAGACTTTTACCTTATGACAATCGGCTGGTATAATGCCTCTACTTCCAGAGA

CAGACATAAGGAGATTACGCATG

SEQ ID NO.8: Promoter region for pCyn-v8-GFP
GGAGAGTTCCTCATTACCGTTATCATATGAACACACCATAAGGAAGATGCATGCAGCTGTCT

AAATCCCGCGGCCATGGCGGCCGGGAGCATGCGACGTCGGGCCCAATTCGCCCGATCTTAAT

GAATGGCCGGAAGAGGTACGGACGCGATATGCGGGGGTGAGAGGGCAAATAGGCAGGTTCGC

CTTCGTCACGCTAGGAGGCAATTCTATAAGGATCCTCGCAACCTATAAGTAAATCCAATGGA

ACTCGTCAGAAATGAGACTTTTACCTTATGACAATCGGCTGGTATAATGCCTCTACTTCCAG

AGACAGACATAAGGAGATTACGCATG

TABLE 1

| SEQ ID NO. | Primer name | Sequence |
|---|---|---|
| 9. | k1 | TGATAAGCGTAGCGCATCAGGCAATTCCAGCCGCAGACCTGTGTCAGCGGGTGTAGG CTGGAGCTGCTTCGAAG |
| 10. | k2 | TCTACATTAGCCGCATCCGGCATGAACAAAGCGCAGGAACAAGCGTCGCACATATGA ATATCCTCCTTAGTTCC |
| 11. | p1 | AACCAGGATAATGATACAGATTAAATCAGAACGCAGAAG |
| 12. | p2 | TTGTAATCGATAACGTAAATGCATGCCGCTTC |
| 13. | p3 | GCATTTACGTTATCGATTACAAACGTTGAACGAC |
| 14. | p4 | AATCTGTATCATTATCCTGGTTCTTTCCCCCA |
| 15. | p5 | CGGTGGCAGCTCCAAAGGTGAAGAACTG |
| 16. | p6 | AATGAGGAACCATGCTCTCTCGACATATC |
| 17. | p7 | CGAGAGAGCATGGTTCCTCATTACCGTTATCATATG |
| 18. | p8 | CCTTTGGAGCTGCCACCGCCATG |
| 19. | p9 | CGGGCCCAATTCGGGATCCTCGCAACCTATAAGTAAATCC |
| 20. | p10 | CGAGGATCCCGAATTGGGCCCGACGTC |
| 21. | p11 | CGCTAAACTGGGATCCTCGCAACCTATAAGT |
| 22. | p12 | GTACGGTCCAATCTTATAGAATTGCCTCCTAGCGTG |
| 23. | p13 | CAATTCTATAAGATTGGACCGTACGCATGTC |
| 24. | p14 | GCGAGGATCCCAGTTTAGCGATACCACACCA |
| 25. | p15 | ATGAACACACCATAAGGAAGATGCATGCAGCT |
| 26. | p16 | AGCTGCATGCATCTTCCTTATGGTGTGTTCAT |
| 27. | p17 | GTTATCATATGAACACGCCATAAGGAAGATGCA |
| 28. | p18 | TGCATCTTCCTTATGGCGTGTTCATATGATAAC |
| 29. | p19 | CATATGAACACACCATAAGGAAAAGATGCATGCAGCTGTC |
| 30. | p20 | GACAGCTGCATGCATCTTTTCCTTATGGTGTGTTCATATG |
| 31. | p21 | AGAGTTCCTCATTACCGTTATCATATG |
| 32. | p22 | CTCTCCATGCTCTCTCGACATATC |

| SEQ ID NO. | DNA fragment name | Sequence |
|---|---|---|
| 33. | gblock1 | ATCGATTACAAACGTTGAACGACTGGGTTACAGCGAGCTTAGTTTATGCCGGA TGCGGCGTGAACGCCTTATCCGGCCTACGTAGAGCACTGAACTCGTAGGCCTG ATAAGCGTAGCGCATCAGGCAATTCCAGCCGCTGATCTGTGTCAGCGGCTACC GTGATTCATTCCCGCCAACAACCGCGCATTCCTCCAACGCCATGTGCAAAAAT GCCTTCGCAGCGGCTGTCTGCCAGCTGTAGTTTATGCCGGATGCGGCGTGAAC GCCTTATCCGGCCTACGTAGAGCACTGAACTCGTAGGCCTGATAAGCGTAGCG CATCAGGCAATTCCAGCCGCAGACCTGTGTCAGCGGCTACCGTGATTCATTTC CGCCAACAACCGCGCATTTATCCAACGCCATGTGCAAAAATGCCTTCGCGGCG GCTGTCTGCCAGCTATTTTTCCGCCGCAACAAAACCGCCGTTCTCTCCAGTAG TGGCGGGGCAAGAGAAATAGCTTTAAGCCCGTCATGTTGTGTGGCAATCGCTG CTGGTAACAATGTGGAAAGGGAAGTGCGGCGAATCAGCTCCAGAACCGCGCTA ATTGAGTTCGCCTCAATGACCACCTGTGGATGTAGCCCCGCTTTCTCGCAGTA GTGGTCAATTTGCTCTCTGGTGGCAAATTCCGCGCTGAGCAGGACCAGTTTTT CATCATGCAAGCGACTCAACGCCACCTGTTCATGGACGGCCAGCGGATGATGT TGCGCCACGACTAACGCTAAACTTTCTGTCAGTAAAGGAATTGCCTCCAGCTC CGGCGAATGCACAGGCGCGAAGGCAATCCCAACGTCCAACTCGTCGCGGCAAA GCATATCCTCGATTTTCTCCTGCGACATTTCCTGTAGCTGGAGCGTGATGCTG GGATAGCGCGCATAGAAATCCGCCATTAAGGGGCCGATAAAGTAGCTCGTAAA GGTGGGGGTGACGGCGATACGCAGCGATCCTCGCGTCAGATCGGCAACATCAT GAATCGCCCGTTTACCCGCCCCCAGTTCCTGTAACGCCCGGCTGGCGTACTGT CGCCAGACTTCTCCTGCATCAGTGAGACGAATCGTTCGCCCGCTACGGTCAAA CAGCGGCACGCCTAAACTCTCCTCTAACTGGCGAATCTGCTGGGAAAGCGCAG |

TABLE 1-continued

```
                    GTTGGGGAGACGTGCAACGCACTGGCGGCACGGGTGAAGCTGCCATGTTCAGCC
                    ACGGCAAGAAAATAATTGATATGTCGAGAGAGCATTCGCAACCTATAAGTAAA
                    TCCAATGGAACTCATCATAAATGAGACTTTTACCTTATGACAATCGGCGAGTA
                    GTCTGCCTCTCATTCCAGAGACAGACAGAGGTTAACGATG 34.   gblock2     GGTTCCTCATTACCGTTATCATATGAACACACCATAACAAAGATGCATGCAGC
                    TGTCTAAATCCCGCGGCCATGGCGGCCGGGAGCATGCGACGTCGGGCCCAATT
                    CGCCCGATCTTAATGAATGGCCGGAAGAGGTACGGACGCGATATGCGGGGGTG
                    AGAGGGCAAATAGGCAGGTTCGCCTTCGTCACGCTAGGAGGCAATTCTATAAG
                    GATCCTCGCAACCTATAAGTAAATCCAATGGAACTCGTCAGAAATGAGACTTT
                    TACCTTATGACAATCGGCTGGTATAATGCCTCTACTTCCAGAGACAGACATAA
                    GGAGATTACGCATGCATCACCATCATCACCATCACCATGGCGGTGGCAGC 35.   gblock3     GATTGGACCGTACGCATGTCAAACTGCTGGCGAACCGCGATTCCACGACCGGT
                    GCACGATTTAACTACGCCGACGTGACGACATTCCTGCTAATGCCTCGCCCGCC
                    GGACCGCCCTCGTGATGGGGTAGCTGGGCATGACCTTGTGACATATAACGAGA
                    GTCTACTTGTTTAATCATCTCACGGCGAAAGTCGGGGGGACAGCAGCCGCTGC
                    AGACATTATACCGCAACTACACCAAGCTGAGATAACTCCGTAGTTGACTACGC
                    ATCCCTCTAGGCCTTACTTAACCGGATACAGTGACTTTGACAGGTTTGTGGGC
                    TACAGCAATCACTTGCATAGCTGCGTATGGAGGAAGCAACTCTTGGGTGTTAG
                    TATGTTGACCCCTGTATTAGGGATGCGGGTAGTAGATGTGGGCAGAGACACCC
                    AGGTCAAGTACACGACCCTCTCGTAGGAGGTGTTCCAGATCACCATACCACCA
                    TACCATTCGAGCATGGCACTATGTACGCTGTCCCCATTCTGGTAGTCATCATC
                    CCTATCACGGTTTCGAGTGACTGGTGACGGATATCCCCCACGAATGGAGATCT
                    TATTCACAGTCGGTCACATTGGAGTGCTCCTTGACTAATCAGCTTGGCCAGGT
                    CTGTTGGGCCTCCGTGCCCCGAGTTTCGGCGCTGTGCTGCCGAGAGTCGGCCA
                    TTGTCATTGGGGCCTCACTTGTGGATACCCCGACCTATTTTGACGGGACCACT
                    CGCGGTAGTCGTTGGGCTTATGCACCGTGAAGTCCTCCGCCGGCCTCCCCCCT
                    ACAAAAGATGATAAGCTCCGGCAAGCAATATTGAACAACGCAAGGATCGGCGA
                    TATAAACAGAGAAACGGCTGATTACTCTTGTTGGTGTGGTATCGCTAAACTG
```

SEQ ID NO.36: pCyn-V2-GFP Cyn promoter
TCGCAACCTATAAGTAAATCCAATGGAACTCGTCAGAAATGAGACTTTTACCTTATGACAAT

CGGC[TGGTATAAT]GCCTCTACTTCCAGAGACAGACATAAGGAGATTACGCATG

SEQ ID NO.37: pCyn-V2-GFP CynR promoter

TAGACAGCTGCATGCATCTT[TGTTATGGT]GTGTTCATATGATAACGGTAATGAGGAACCATG

SEQ ID NO.38: pCyn-V8-GFP Cyn promoter
TCGCAACCTATAAGTAAATCCAATGGAACTCGTCAGAAATGAGACTTTTACCTTATGACAAT

CGGC[TGGTATAAT]GCCTCTACTTCCAGAGACAGACATAAGGAGATTACGCATG

SEQ ID NO.39: pCyn-V8-GFP CynR promoter

TAGACAGCTGCATGCATCTTCCT[TATGGT]GTGTTCATATGATAACGGTAATGAGGAA*CTCT*C

CATG

Enumerated Embodiments

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

Embodiment 1 provides a construct comprising
  a. a cyn promoter comprising an engineered −10 sequence and a consensus ribosome binding sequence; which is linked to
  b. a cynR promoter comprising an engineered −10 sequence, wherein the engineered −10 sequences comprise at least one nucleotide addition, subtraction, and/ or mutation that improves protein expression from the respective promoters.

Embodiment 2 provides the construct of Embodiment 1, wherein the cyn promoter and the independent constitutive promoter are separated by a spacer comprising about 10 to about 1000 nucleotides.

Embodiment 3 provides the construct of any of Embodiments 1-2, where in the cyn promoter and the independent constitutive promoter are directly linked to each other.

Embodiment 4 provides the construct of any of Embodiments 1-3, wherein the constitutive cynR promoter is further engineered to regulate the expression of CynR protein.

Embodiment 5 provides the construct of any of Embodiments 1-4, wherein the construct comprises nucleic acid sequence selected from the group consisting of SEQ ID NOs: 2-8.

Embodiment 6 provides a plasmid vector comprising:
  a. the construct of Embodiment 1;
  b. an ampicillin resistance gene; and c. a gene encoding a protein of interest, wherein the gene is located downstream of the cyn promoter;

wherein the expression of the gene encoding the protein of interest is inducible by azide or cyanate.

Embodiment 7 provides the plasmid vector of Embodiment 6, wherein the construct comprises a sequence selected from the group consisting of SEQ ID NO: 2 and SEQ ID NO: 8.

Embodiment 8 provides the plasmid vector of any of Embodiments 6-7, wherein the protein of interest is a reporter protein.

Embodiment 9 provides the plasmid vector of Embodiment 8, wherein the reporter protein is a GFP.

Embodiment 10 provides an inducible protein expression system for a enhancing the expression of a protein of interest, wherein the protein expression system comprises a host cell transformed with the plasmid vector of any of Embodiments 6-8.

Embodiment 11 provides the protein expression system of Embodiment 10, wherein the host cell is an *E. coli* cell selected from the group consisting of BW25113, BW25113-sCB1, BW25113-sKS3, and BW25113-sKS4.

Embodiment 12 provides the protein expression system of any of Embodiments 10-11, wherein expression of the protein of interest is enhanced by about 20 fold to about 180 fold relative to the protein expression system comprising the native cyn promoter.

Embodiment 13 provides the protein expression system of any of Embodiments 10-12, wherein the protein of interest is a reporter protein.

Embodiment 14 provides the protein expression system of Embodiment 13, wherein the reporter protein is a GFP.

Embodiment 15 provides a tunable synthetic biosensor for in vivo detection of an inorganic azide, wherein the biosensor comprises the protein expression system of any of Embodiments 10-14.

Embodiment 16 provides a method of screening activity and specificity of an enzyme in an enzymatic reaction that generates an azide ion, wherein the method comprises:

a. contacting the biosensor of Embodiment 15 with the azide ion generated during the enzymatic reaction, wherein the protein of interest is a reporter protein; and b. quantifying a signal generated from the reporter protein;

wherein, the quantified signal is positively correlated with the activity and the specificity of the enzyme.

Embodiment 17 provides the method of Embodiment 16, wherein the enzyme is a carbohydrate active enzyme.

Embodiment 18 provides the method of Embodiment 17, wherein the carbohydrate active enzyme is selected from the group consisting of glycosyl hydrolase and transglycosidase.

Embodiment 19 provides the method of any of Embodiments 16-18, wherein the enzymatic reaction is a glycosynthase reaction that uses at least one of a glycosyl azide and a fucosyl azide as a donor sugar.

Embodiment 20 provides the method of any of Embodiments 16-19, wherein the reporter protein is a GFP.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

---

What is claimed is:

1. A construct comprising a cyn promoter and a cynR promoter, wherein the construct comprises a nucleic acid sequence selected from the group consisting of SEQ ID NOs: 2 and 8.

2. A plasmid vector comprising:
   a. the construct comprising a cyn promoter and a cynR promoter, wherein the construct comprises a nucleic acid sequence selected from the group consisting of SEQ ID NOs: 2 and 8;
   b. an ampicillin resistance gene;
   c. a gene encoding a protein of interest, wherein the gene is located downstream of the cyn promoter; and
   d. a cynR gene, wherein the cynR gene is located downstream of the cynR promoter, wherein the expression of the gene encoding the protein of interest is inducible by azide.

3. The plasmid of claim 2, wherein the protein of interest is a reporter protein.

4. The plasmid of claim 3, wherein the reporter protein is a green fluorescent protein (GFP).

5. An inducible protein expression system for enhancing the expression of a protein of interest, wherein the protein expression system comprises a host cell transformed with the plasmid vector of claim 2.

6. The protein expression system of claim 5, wherein the host cell is an *E. coli* cell selected from the group consisting of BW25113, BW25113-sCB1, BW25113-sKS3, and BW25113-sKS4.

7. The protein expression system of claim 5, wherein the protein of interest is a reporter protein.

8. The protein expression system of claim 7, wherein the reporter protein is a GFP.

9. A tunable synthetic biosensor for in vivo detection of an inorganic azide, wherein the biosensor comprises the inducible protein expression system of claim 5.

10. A method of screening activity and specificity of an enzyme in an enzymatic reaction that generates an azide ion, wherein the method comprises:
    a. contacting the biosensor of claim 9 with the azide ion generated during the enzymatic reaction, wherein the protein of interest is a reporter protein; and
    b. quantifying a signal generated from the reporter protein;
    wherein the quantified signal is positively correlated with the activity and the specificity of the enzyme.

11. The method of claim 10, wherein the enzyme is a carbohydrate active enzyme.

12. The method of claim 11, wherein the carbohydrate active enzyme is selected from the group consisting of glycosyl hydrolase and transglycosidase.

13. The method of claim 10, wherein the enzymatic reaction is a glycosynthase reaction that uses at least one of a glycosyl azide and a fucosyl azide as a donor sugar.

14. The method of claim 10, wherein the reporter protein is a GFP.

* * * * *